(12) United States Patent  (10) Patent No.: US 7,726,002 B2
Shimp et al.  (45) Date of Patent: Jun. 1, 2010

(54) PROCESSES FOR MAKING SPINAL INTERVERTEBRAL IMPLANT, INTERCONNECTIONS FOR SUCH IMPLANT

(75) Inventors: Lawrence A. Shimp, Morganville, NJ (US); John M. Winterbottom, Jackson, NJ (US); David R. Kaes, Toms River, NJ (US); Todd M. Boyce, Aberdeen, NJ (US); Erik O. Martz, Howell, NJ (US)

(73) Assignee: Osteotech, Inc., Eatontown, NJ (US)

( * ) Notice: Subject to any disclaimer, the term of this patent is extended or adjusted under 35 U.S.C. 154(b) by 1511 days.

(21) Appl. No.: 10/964,113

(22) Filed: Oct. 13, 2004

(65) Prior Publication Data
US 2005/0107880 A1    May 19, 2005

Related U.S. Application Data

(62) Division of application No. 10/005,238, filed on Dec. 5, 2001, now Pat. No. 6,855,167.

(51) Int. Cl.
*B23P 17/00*    (2006.01)
*A61F 2/44*    (2006.01)

(52) U.S. Cl. .................. 29/525.01; 623/17.11

(58) Field of Classification Search .......... 29/525.01, 29/525.03, 525.04, 525.05, 464, 428; 623/17.11, 623/16.11, 23.63, 919; 403/408.1, 13, 14; 606/76
See application file for complete search history.

(56) References Cited

U.S. PATENT DOCUMENTS

| | | | |
|---|---|---|---|
| 1,025,008 A | 4/1912 | Miner | |
| 2,375,116 A | 5/1945 | Larkin | 189/36 |
| 2,525,222 A | 10/1950 | Holt | |
| 3,068,916 A | 12/1962 | Richardson | 144/12 |
| 3,486,505 A | 12/1969 | Morrison | |
| 3,604,298 A | 9/1971 | Dekiel | 83/694 |
| 3,604,487 A | 9/1971 | Gilbert | |
| 3,703,006 A | 11/1972 | Bokros et al. | |

(Continued)

FOREIGN PATENT DOCUMENTS

AU   744371   11/1998

(Continued)

OTHER PUBLICATIONS

Albee, Fred H., "Bone Surgery with Machine Tools," *Scientific American*, Apr. 1936, pp. 178-181.

(Continued)

*Primary Examiner*—John C Hong
(74) *Attorney, Agent, or Firm*—Kenneth E. Levitt; Dorsey & Whitney LLP

(57) ABSTRACT

A cortical bone implant is formed of two or more planks of bone which are connected with one or more offset pins. The pins may be right circular cylinders inserted into a corresponding offset bore which offset bends the inserted pin. The bending creates compression and tensile loads in the pin which loads creates friction compression forces on the planks connecting them to the pins by friction. The pins may have different shapes to form offset configurations in place of the offset bores for friction attachment to the planks. The implants may be formed of flat or L-shaped planks or bones formed into other shapes including interlocking arrangements. Processes and fixtures are disclosed for forming the pins, planks and implants. Various embodiments of the pins, planks, implants and processes are disclosed.

9 Claims, 21 Drawing Sheets

U.S. PATENT DOCUMENTS

| | | | |
|---|---|---|---|
| 3,848,601 A | 11/1974 | Ma et al. | |
| 4,033,244 A | 7/1977 | Jacobson | |
| 4,059,115 A | 11/1977 | Jumashev et al. | |
| 4,185,383 A | 1/1980 | Heimke et al. | |
| 4,273,117 A | 6/1981 | Neuhauser | |
| 4,349,921 A | 9/1982 | Kuntz | |
| 4,394,370 A | 7/1983 | Jefferies | |
| 4,416,278 A | 11/1983 | Miller | |
| 4,440,750 A | 4/1984 | Glowacki et al. | |
| 4,484,570 A | 11/1984 | Sutter et al. | |
| 4,485,097 A | 11/1984 | Bell | |
| 4,516,276 A | 5/1985 | Mittelmeier et al. | |
| 4,553,575 A | 11/1985 | Brown | |
| 4,559,936 A | 12/1985 | Hill | |
| 4,566,466 A | 1/1986 | Ripple et al. | |
| 4,573,448 A | 3/1986 | Kambin | |
| 4,637,931 A | 1/1987 | Schmitz | |
| 4,649,918 A | 3/1987 | Pegg et al. | |
| 4,678,470 A | 7/1987 | Nashef et al. | |
| 4,714,469 A | 12/1987 | Kenna | |
| 4,743,256 A | 5/1988 | Brantigan | |
| 4,743,259 A | 5/1988 | Bolander et al. | |
| 4,753,235 A | 6/1988 | Hasson | |
| 4,772,287 A | 9/1988 | Ray et al. | |
| 4,782,833 A | 11/1988 | Einhorn | |
| 4,798,213 A | 1/1989 | Doppelt | |
| 4,820,305 A | 4/1989 | Harms et al. | |
| 4,834,757 A | 5/1989 | Brantigan | |
| 4,863,477 A | 9/1989 | Monson | |
| 4,877,020 A | 10/1989 | Vich | |
| 4,878,915 A | 11/1989 | Brantigan | |
| 4,904,261 A | 2/1990 | Dove et al. | |
| 4,917,704 A | 4/1990 | Frey et al. | |
| 4,932,973 A | 6/1990 | Gendler | |
| 4,938,768 A | 7/1990 | Wu | 623/16 |
| 4,950,296 A | 8/1990 | McIntyre | |
| 4,955,885 A | 9/1990 | Meyers | |
| 4,961,740 A | 10/1990 | Ray et al. | |
| 4,963,154 A | 10/1990 | Anapliotis et al. | |
| 4,997,434 A | 3/1991 | Seedhom et al. | |
| 5,015,247 A | 5/1991 | Kuslich | |
| 5,015,255 A | 5/1991 | Kuslich | |
| 5,026,373 A | 6/1991 | Ray et al. | |
| 5,047,058 A | 9/1991 | Roberts et al. | |
| 5,049,150 A | 9/1991 | Cozad | |
| 5,053,049 A | 10/1991 | Campbell | |
| 5,055,104 A | 10/1991 | Ray | |
| 5,061,786 A | 10/1991 | Burnier et al. | |
| 5,062,845 A | 11/1991 | Kuslich et al. | |
| 5,112,354 A | 5/1992 | Sires | |
| 5,171,278 A | 12/1992 | Pisharodi | |
| 5,192,321 A | 3/1993 | Strokon | |
| 5,192,327 A | 3/1993 | Brantigan | |
| 5,197,967 A | 3/1993 | Wilson | |
| 5,207,710 A | 5/1993 | Chu et al. | |
| 5,236,456 A | 8/1993 | O'Leary et al. | |
| 5,284,655 A | 2/1994 | Bogdansky et al. | |
| 5,298,254 A | 3/1994 | Prewett et al. | |
| 5,306,307 A | 4/1994 | Senter et al. | |
| 5,306,308 A | 4/1994 | Gross et al. | |
| 5,306,309 A | 4/1994 | Wagner et al. | |
| 5,306,310 A | 4/1994 | Siebels | |
| 5,312,408 A | 5/1994 | Brown | |
| 5,314,476 A | 5/1994 | Prewett et al. | |
| 5,314,478 A | 5/1994 | Oka et al. | |
| 5,361,483 A | 11/1994 | Rainville et al. | 29/524.1 |
| 5,380,333 A | 1/1995 | Meloul et al. | |
| 5,390,683 A | 2/1995 | Pisharodi | |
| 5,397,364 A | 3/1995 | Kozak et al. | |
| 5,423,817 A | 6/1995 | Lin | |
| 5,423,825 A | 6/1995 | Levine | |
| 5,425,772 A | 6/1995 | Brantigan | |
| 5,425,773 A | 6/1995 | Boyd et al. | |
| 5,439,684 A | 8/1995 | Prewett et al. | |
| 5,443,514 A | 8/1995 | Steffee | |
| 5,445,639 A | 8/1995 | Kuslich et al. | |
| 5,458,638 A | 10/1995 | Kuslich et al. | |
| 5,458,643 A | 10/1995 | Oka et al. | |
| 5,484,437 A | 1/1996 | Michelson | |
| 5,489,307 A | 2/1996 | Kuslich et al. | |
| 5,489,308 A | 2/1996 | Kuslich et al. | |
| 5,490,962 A | 2/1996 | Cima et al. | |
| 5,505,731 A | 4/1996 | Tornier | |
| 5,505,732 A | 4/1996 | Michelson | |
| 5,507,813 A | 4/1996 | Dowd et al. | |
| 5,514,180 A | 5/1996 | Heggeness et al. | |
| 5,518,680 A | 5/1996 | Cima et al. | |
| 5,522,899 A | 6/1996 | Michelson | |
| 5,534,028 A | 7/1996 | Bao et al. | |
| 5,534,030 A | 7/1996 | Navarro et al. | |
| 5,545,222 A | 8/1996 | Bonutti | |
| 5,554,191 A | 9/1996 | Lahille et al. | |
| 5,562,738 A | 10/1996 | Boyd et al. | |
| 5,571,190 A | 11/1996 | Ulrich et al. | |
| 5,571,192 A | 11/1996 | Schonhoffer | |
| 5,591,235 A | 1/1997 | Kuslich | |
| 5,593,409 A | 1/1997 | Michelson | |
| 5,607,269 A | 3/1997 | Dowd et al. | |
| 5,607,424 A | 3/1997 | Tropiano | |
| 5,609,635 A | 3/1997 | Michelson | |
| 5,609,636 A | 3/1997 | Kohrs et al. | |
| 5,632,747 A | 5/1997 | Scarborough et al. | |
| 5,645,596 A | 7/1997 | Kim et al. | |
| 5,645,598 A | 7/1997 | Brosnahan, III | |
| 5,653,761 A | 8/1997 | Pisharodi | |
| 5,653,762 A | 8/1997 | Pisharodi et al. | |
| 5,653,763 A | 8/1997 | Errico et al. | |
| 5,658,336 A | 8/1997 | Pisharodi | |
| 5,658,337 A | 8/1997 | Kohrs et al. | |
| 5,662,710 A | 9/1997 | Bonutti | |
| 5,669,909 A | 9/1997 | Zdeblick et al. | |
| 5,683,394 A | 11/1997 | Rinner | |
| 5,683,463 A | 11/1997 | Godefroy et al. | |
| 5,683,464 A | 11/1997 | Wagner et al. | |
| 5,702,391 A | 12/1997 | Lin | |
| 5,707,371 A | 1/1998 | Metz-Stavenhagen | |
| 5,709,683 A | 1/1998 | Bagby | |
| 5,716,415 A | 2/1998 | Steffee | |
| 5,716,416 A | 2/1998 | Lin | |
| 5,720,751 A | 2/1998 | Jackson | |
| 5,728,159 A | 3/1998 | Stroever et al. | |
| 5,741,253 A | 4/1998 | Michelson | |
| 5,749,916 A | 5/1998 | Richelsoph | |
| 5,766,251 A | 6/1998 | Koshino | |
| 5,766,252 A | 6/1998 | Henry et al. | |
| 5,769,897 A | 6/1998 | Harle | |
| 5,776,199 A | 7/1998 | Michelson | |
| 5,782,830 A | 7/1998 | Farris | |
| 5,782,919 A | 7/1998 | Zdeblick et al. | |
| 5,785,710 A | 7/1998 | Michelson | |
| 5,800,547 A | 9/1998 | Schafer et al. | |
| 5,807,437 A | 9/1998 | Sachs et al. | |
| 5,814,084 A | 9/1998 | Grivas et al. | |
| 5,824,078 A | 10/1998 | Nelson et al. | |
| 5,824,094 A | 10/1998 | Serhan et al. | |
| 5,846,484 A | 12/1998 | Scarborough et al. | |
| 5,860,973 A | 1/1999 | Michelson | |
| 5,865,845 A | 2/1999 | Thalgott | |
| 5,868,749 A | 2/1999 | Reed | |
| 5,885,299 A | 3/1999 | Winslow et al. | |
| 5,885,300 A | 3/1999 | Tokuhashi et al. | |
| 5,888,219 A | 3/1999 | Bonutti | |
| 5,888,222 A | 3/1999 | Coates | |
| 5,888,227 A | 3/1999 | Cottle | |

| | | |
|---|---|---|
| 5,895,426 A | 4/1999 | Scarborough et al. |
| 5,895,428 A | 4/1999 | Berry |
| 5,899,939 A | 5/1999 | Boyce et al. |
| 5,904,683 A | 5/1999 | Pohndorf et al. |
| 5,904,719 A | 5/1999 | Errico et al. |
| 5,928,238 A | 7/1999 | Scarborough et al. |
| 5,941,882 A | 8/1999 | Jammet et al. |
| 5,968,047 A | 10/1999 | Reed |
| 5,972,368 A | 10/1999 | McKay |
| 5,980,522 A | 11/1999 | Koros et al. |
| 5,984,967 A | 11/1999 | Zdeblick et al. |
| 5,989,289 A | 11/1999 | Coates et al. |
| 6,025,538 A | 2/2000 | Yaccarino, III |
| 6,030,635 A | 2/2000 | Gertzman et al. |
| 6,045,554 A | 4/2000 | Grooms et al. |
| 6,045,579 A | 4/2000 | Hochshuler et al. |
| 6,045,580 A | 4/2000 | Scarborough et al. |
| 6,066,174 A | 5/2000 | Farris |
| 6,077,267 A | 6/2000 | Huene |
| 6,083,225 A | 7/2000 | Winslow et al. |
| 6,090,143 A | 7/2000 | Meriwether et al. |
| 6,096,081 A | 8/2000 | Grivas et al. |
| 6,102,950 A | 8/2000 | Vaccaro |
| 6,111,164 A | 8/2000 | Rainey et al. |
| 6,113,637 A | 9/2000 | Gill et al. |
| 6,113,638 A | 9/2000 | Williams et al. |
| 6,123,705 A | 9/2000 | Michelson |
| 6,123,731 A | 9/2000 | Boyce et al. ............ 623/23.63 |
| 6,132,472 A | 10/2000 | Bonutti |
| 6,136,002 A | 10/2000 | Shih et al. |
| 6,139,211 A * | 10/2000 | Schroeder et al. ............ 403/13 |
| 6,143,033 A | 11/2000 | Paul et al. |
| 6,156,037 A | 12/2000 | LeHuec et al. |
| 6,159,215 A | 12/2000 | Urbahns et al. |
| 6,174,311 B1 | 1/2001 | Branch et al. ................ 606/61 |
| 6,200,347 B1 | 3/2001 | Anderson et al. ........ 623/16.11 |
| 6,206,923 B1 | 3/2001 | Boyd et al. |
| 6,210,442 B1 | 4/2001 | Wing et al. |
| 6,235,059 B1 | 5/2001 | Benezech et al. |
| 6,258,125 B1 | 7/2001 | Paul et al. |
| 6,270,528 B1 | 8/2001 | McKay |
| 6,277,149 B1 | 8/2001 | Boyle et al. ............ 623/17.16 |
| 6,294,041 B1 | 9/2001 | Boyce et al. |
| 6,294,187 B1 | 9/2001 | Boyce et al. |
| 6,315,795 B1 | 11/2001 | Scarborough et al. |
| 6,326,018 B1 | 12/2001 | Gertzman et al. |
| 6,350,283 B1 | 2/2002 | Michelson |
| 6,379,385 B1 | 4/2002 | Kalas et al. |
| 6,383,221 B1 | 5/2002 | Scarborough et al. |
| 6,425,920 B1 | 7/2002 | Hamada |
| 6,432,107 B1 | 8/2002 | Ferree |
| 6,454,806 B1 | 9/2002 | Cohen et al. |
| 6,468,543 B1 | 10/2002 | Gilbertson et al. |
| 6,527,773 B1 | 3/2003 | Lin et al. |
| 6,530,955 B2 | 3/2003 | Boyle et al. |
| 6,547,823 B2 | 4/2003 | Scarborough et al. |
| 6,569,168 B2 | 5/2003 | Lin |
| 6,579,321 B1 | 6/2003 | Gordon et al. |
| 6,638,310 B2 | 10/2003 | Lin et al. |
| 6,696,073 B2 | 2/2004 | Boyce et al. |
| 6,733,504 B2 | 5/2004 | Lin et al. |
| 6,855,167 B2 | 2/2005 | Shimp et al. |
| 6,863,694 B1 | 3/2005 | Boyce et al. |
| 6,911,045 B2 | 6/2005 | Shimp |
| 2001/0020186 A1 | 9/2001 | Boyce et al. |
| 2001/0043258 A1 | 11/2001 | Ohki |
| 2002/0029084 A1 | 3/2002 | Paul et al. |
| 2002/0045897 A1 | 4/2002 | Dixon et al. |
| 2002/0058950 A1 | 5/2002 | Winterbottom et al. |
| 2002/0128717 A1 | 9/2002 | Alfaro et al. |
| 2002/0161445 A1 | 10/2002 | Crozel |
| 2002/0188295 A1 | 12/2002 | Martz et al. |
| 2003/0039676 A1 | 2/2003 | Boyce et al. |
| 2003/0049326 A1 | 3/2003 | Nimni |
| 2003/0060825 A1 | 3/2003 | Alfaro et al. |
| 2003/0130667 A1 | 7/2003 | Lin |
| 2003/0135214 A1 | 7/2003 | Fetto et al. |
| 2003/0147860 A1 | 8/2003 | Marchosky |
| 2004/0024457 A1 | 2/2004 | Boyce et al. |
| 2004/0044409 A1 | 3/2004 | Alfaro et al. |
| 2004/0098129 A1 | 5/2004 | Lin |
| 2004/0146543 A1 | 7/2004 | Shimp et al. |
| 2004/0243242 A1 | 12/2004 | Sybert et al. |
| 2004/0249377 A1 | 12/2004 | Kaes et al. |
| 2005/0008620 A1 | 1/2005 | Shimp et al. |
| 2005/0008672 A1 | 1/2005 | Winterbottom et al. |
| 2005/0027033 A1 | 2/2005 | Knaack et al. |
| 2005/0038511 A1 | 2/2005 | Martz et al. |
| 2005/0107880 A1 | 5/2005 | Shimp et al. |
| 2005/0143740 A1 | 6/2005 | Morris et al. |
| 2005/0283255 A1 | 12/2005 | Geremakis et al. |
| 2006/0149376 A1 | 7/2006 | Shimp et al. |
| 2007/0178158 A1 | 8/2007 | Knaack et al. |

FOREIGN PATENT DOCUMENTS

| | | |
|---|---|---|
| DE | 2 253 086 | 10/1972 |
| DE | 40 12 622 C | 7/1991 |
| DE | 43 02 397 | 7/1993 |
| DE | 198 15 407 | 10/1999 |
| DE | 298 14 174 U | 12/1999 |
| EP | 0 302 719 | 2/1989 |
| EP | 0 307 241 | 3/1989 |
| EP | 0 325 566 | 7/1989 |
| EP | 0 332 826 | 9/1989 |
| EP | 0 493 698 | 7/1992 |
| EP | 0 732 093 | 2/1996 |
| EP | 0 734 703 | 10/1996 |
| EP | 1 064 890 | 1/2001 |
| FR | 2636227 | 3/1990 |
| FR | 2703580 | 10/1994 |
| FR | 2742652 | 6/1997 |
| FR | 2769827 | 4/1999 |
| JP | 01/179689 | 7/1989 |
| SE | 106 101 | 12/1942 |
| SU | 1107854 | 8/1984 |
| SU | 590872 A * | 11/1985 ................ 623/16 |
| WO | WO 89/09035 | 10/1989 |
| WO | WO 93/01771 | 2/1993 |
| WO | WO 94/21298 | 9/1994 |
| WO | WO 97/15246 | 5/1997 |
| WO | WO 97/47258 | 12/1997 |
| WO | WO 98/02117 | 1/1998 |
| WO | WO 98/48738 | 11/1998 |
| WO | WO 99/07312 | 2/1999 |
| WO | WO 99/09914 | 3/1999 |
| WO | WO 99/21515 | 5/1999 |
| WO | WO 99/38461 | 8/1999 |
| WO | WO 00/07527 | 2/2000 |
| WO | WO 00/24327 | 5/2000 |
| WO | WO 00/40177 | 7/2000 |
| WO | WO 00/40179 | 7/2000 |
| WO | WO 01/00792 | 1/2001 |
| WO | WO01/49220 | 7/2001 |
| WO | WO 01/66048 | 9/2001 |
| WO | WO01/70136 | 9/2001 |
| WO | WO 01/70137 | 9/2001 |
| WO | WO01/70139 | 9/2001 |
| WO | WO01/78798 | 10/2001 |
| WO | WO 03/030956 A2 | 4/2003 |
| WO | WO 2005/072656 | 8/2005 |

OTHER PUBLICATIONS

*Allograft Freeze-Dried Release Specifications*, Osteotech, Inc., Sep. 30, 1992, 3 pages.

Brantigan, J.W., DePuy AcroMed, Lumbar I/F Cage With VSP Spinal System (Surgical Technique) (1999).

Crowe et al., "Inhibition of Enzymatic Digestion of Amylose by Free Fatty Acids in Vitro Contributes to Resistant Starch Formation", J. Nutr. 130(8): 2006-2008, 2000.

DePuy AcroMed, Lumbar I/F Cage Implants & Instruments (Product Catalog) (1999).

Driessens et al., "Calcium phosphate bone cements," *Universitat Politecnica de Catalunya, Barcelona*, Spain, 31: 855-77.

Edwards et al., "Osteoinduction of Human Demineralized Bone: Characterization in Rat Model", Clinical Orthopaedics and Related Research, No. 357, pp. 219-228 (1998).

Frymoyer et al., Eds., "The Adult Spine Principles and Practice," *Poster Lumbar Interbody Fusion*, James W. Simmons, vol. 2, pp. 1961-1987 (1991).

Gerhart et al. "Biomechanical optimization of a model particulate composite for orthopaedic applications," *J. Orthop. Res* (1986); 4(1): 86-85 [abstract only].

Glowacki et al., "Fate of Mineralized and Demineralized Osseous Implants in Cranial Defects", Calcified Tissue Int. 33: 71-76, 1981.

Glowacki et al., "Demineralized Bone Implants", Symposium on Horizons in Plastic Surgery, vol. 12, No. 2, pp. 233-241 (1985).

Han et al. "Quantitative and sensitive in vitro assay for osteoinductive activity of demineralized bone matrix," J. Orthop. Res., 21(4): 648-54, 2003.

Jain et al., "Anchoring of phospholipase A2: the effect of anions and deuterated water, and the role of N-terminus region," *Biochem. et Biophys. Acta*, 860:448-61, 1986.

Katz, "The biology of heavy water," *Scientific American*, 106-116, 1960.

Lewandrowski et al., "Improved Osteoinduction of Cortical Bone Allografts: A Study of the Effects of Laser Perforation and Partial Demineralization," *J. Ortho Res.* 15:748-756 (1997).

Ma, G.W.C., Posterior Lumbar Interbody Fusion with Specialized Instruments, *Clinical Ortho and Rel. Res.*, 193 (March) pp. 57-63 (1985).

McCord et al., "Anterior endoscopic thoracolumbar instrumentation and implants," *Curr. Ortho 12*, pp. 96-103 (1998).

Neigal et al., "Use of Demineralized Bone Implants in Orbital and Craniofacial", Opthal. Plast. Reconstrs. Surg., 12: 108-120, 1996.

Ray et al., "Preliminary Report of an Experimental Study", J. Bone Joint Surgery, 39 A: 1119-1128, 1957.

Russell et al., "Clinical Utility of Demineralized Bone Matrix for Osseous Defects, Arthrodesis and Reconstruction: Impact of Processing Techniques and Study Methodology", Orthpaedics, 22(5): 524-531, 1999.

Smith, MD et al. "Load-bearing capacity of corticocancellous bone grafts in the spine" (truncated abstract), Aug. 1993, *Journal of Bone & Joint Surgery*, 75(8): 1206-13.

Sofamar Danek, "Surgical Technique Using Bone Dowel Instrumentation for Anterior Approach" [Publication Date Unknown].

Stevenson, S., "Enhancement of Fracture Healing with Autogenous and Allogeneic Bone Grafts," *Clin. Ortho, Rel. Res.* 355S, pp. S239-S246 (1998).

Tan et al., A modified technique of anterior Lumbar fusion with femoral cortical allograft; *J. Orthop. Surg. Tech*; vol. 5, No. 3 91990), pp. 83-93.

Ueland et al., "Increased Cortical Bone Content of Insulin-Like Growth Factors in Acromegalic Patients", J. Clin. Endocrinol. Metab., 84(1): 123-127, 1999.

University of Florida Tissue Bank, Inc., Allograft Catalog [Publication Date Unknown].

University of Florida Tissue Transplant Patient Education Series [Publication Data Unknown].

Urist et al., "Observations implicating an extracellular enzymic mechanism of control of bone morphogenesis," *J. Histochem & Cytochem*, 22(2): 88-103, 1974.

Urist et al., "Preservation and biodegradation of the morphogenetic property of bone matrix," *J. Theor. Biol.* 38: 155-67, 1973.

Urist, "Bone: Formation by Autoinduction", Science, 150: 893-899, 1965.

VG2 Interbody Bone Grafts, DuPuy AcroMed, 2000, 6 pages.

Vich, Jose M. Otero, "Anterior cervical interbody fusion with threaded cylindrical bone," *J. Neurosurg.* 63:750-753, 1985.

Whiteman et al., "Demineralized Bone Powder—Clinical Applications for Bone Defects of the Hand", J. Hand. Surg., 18B: 487-490, 1993.

Whittaker et al., "Matrix Metalloproteinases and Their Inhibitors—Current Status and Future Challenges", Celltransmissions, 17(1): 3-14.

Xiabo et al., "Experimental and Clinical Investigations of Human Insoluble Bone Matrix Gelatin", Clin. Orthrop. 293: 360-365, 1993.

Zhang, et al., "A Quantative Assessment of Osteoinductivity of Human Demineralized Bone Matrix", J. Periodontol. 68(11): 1076-1084, 1997.

\* cited by examiner

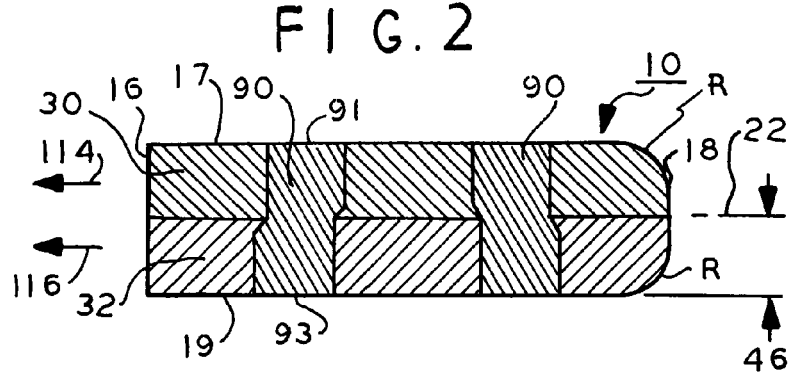
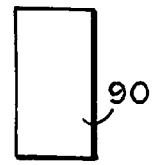
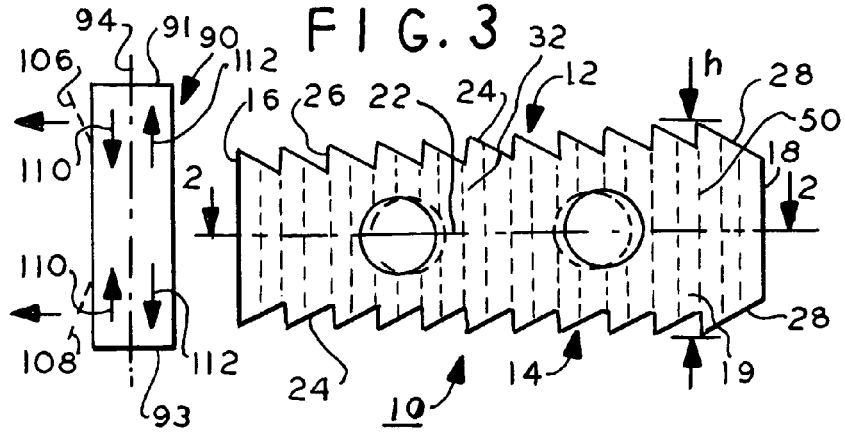
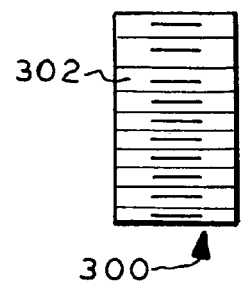
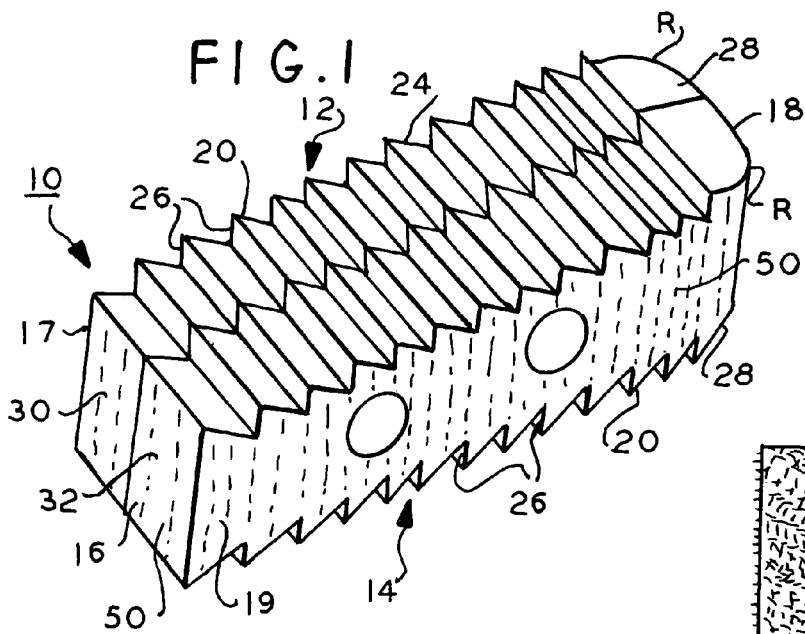
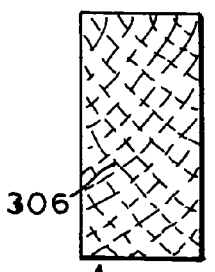

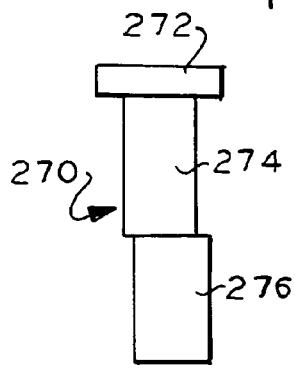
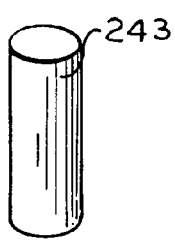
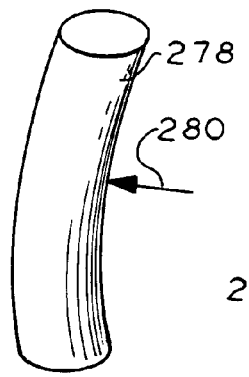
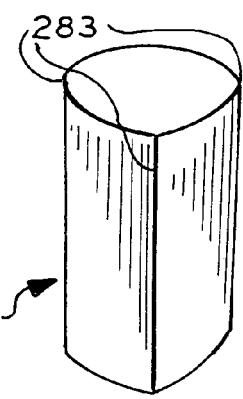
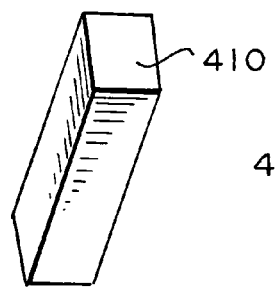
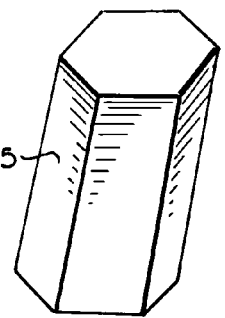
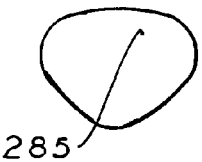
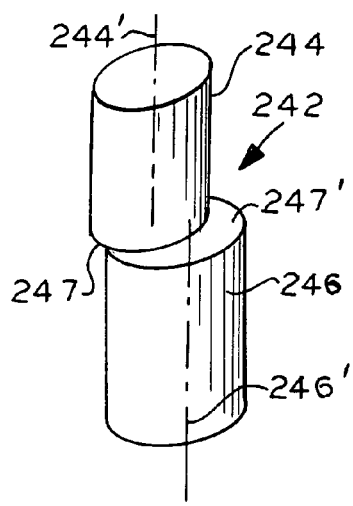
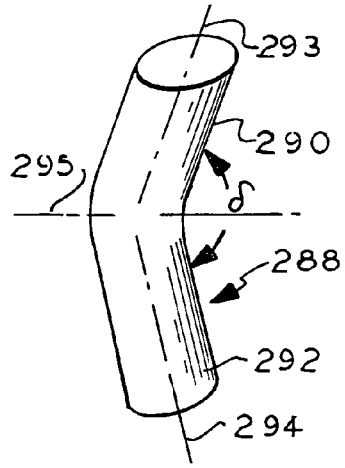
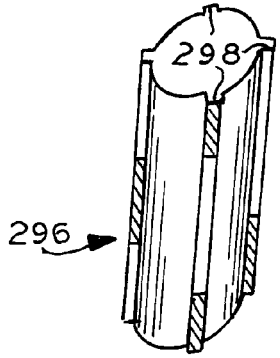
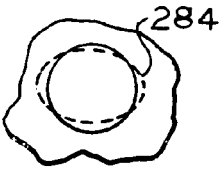

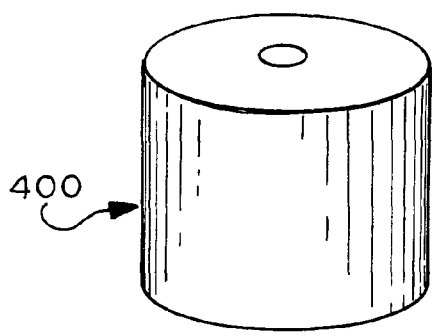
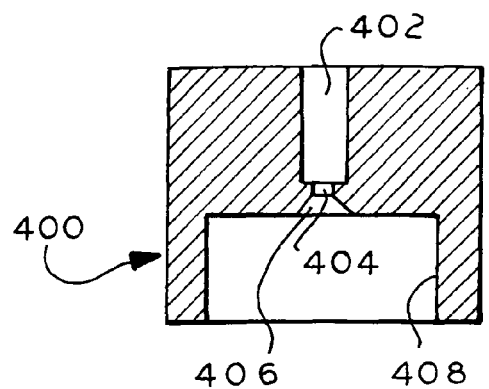
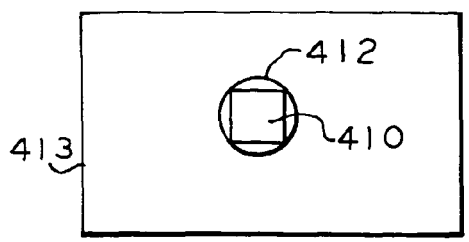
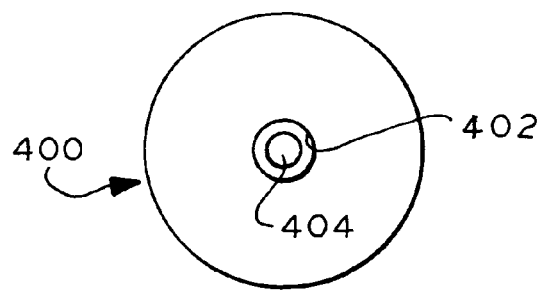
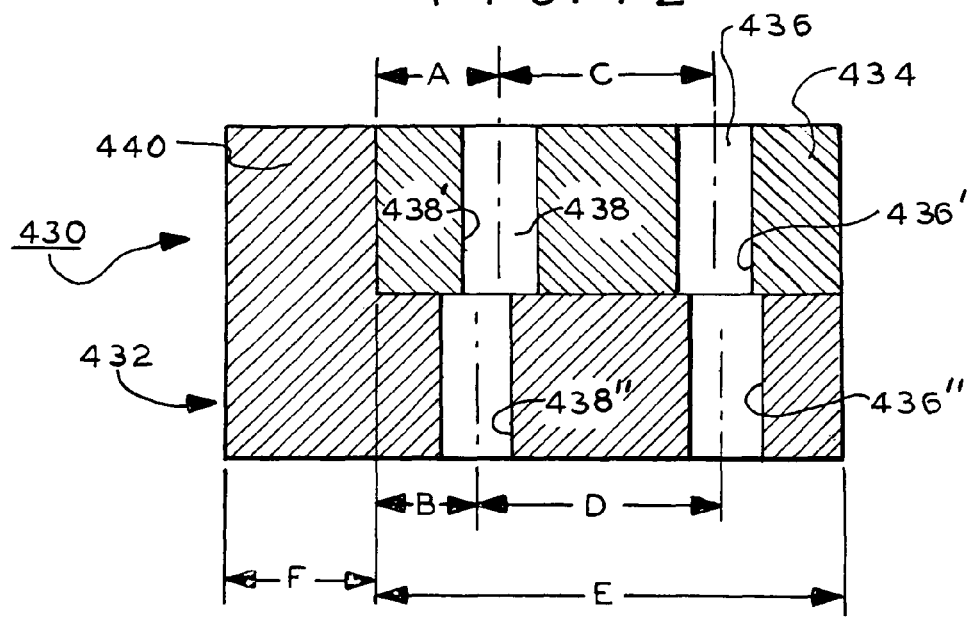

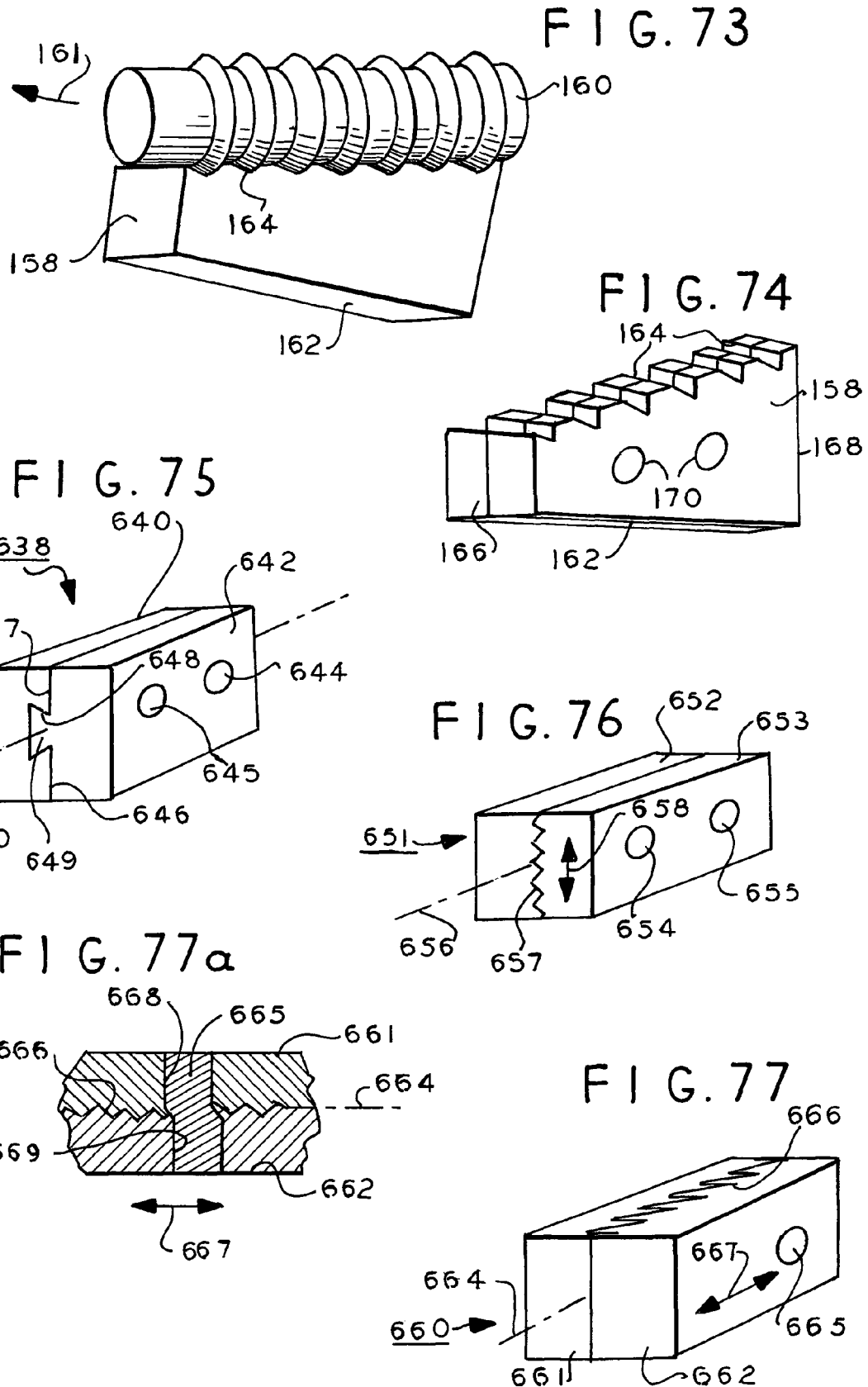

PROCESSES FOR MAKING SPINAL INTERVERTEBRAL IMPLANT, INTERCONNECTIONS FOR SUCH IMPLANT

This application is a divisional of application Ser. No. 10/005,238 filed Dec. 5, 2001, now U.S. Pat. No. 6,855,167, which is incorporated by reference herein in its entirety.

This invention relates to spinal intervertebral fusion implants, processes for making such implants and interconnecting arrangements for attaching bone implants formed from planks of bone.

CROSS REFERENCE TO RELATED APPLICATIONS

Of interest are commonly owned U.S. Pat. No. 6,123,731 to Boyce et al. and U.S. Pat. No. 5,899,939 to Boyce et al. and copending application Ser. No. 09/705,377 entitled Spinal Intervertebral Implant filed Nov. 3, 2000 corresponding to PCT/US01/45551 filed Nov. 2, 2001, Ser. No. 09/328,242 entitled Ramp Shaped Intervertebral Implant filed Jun. 8, 1999 in the name of John W. Boyle, now U.S. Pat. No. 6,277,149, Ser. No. 60/246,297 entitled Spinal Intervertebral Insertion Tool filed Nov. 7, 2000 in the name of Erik Martz et al. and corresponding to PCT application PCT/US01/44414, filed Nov. 6, 2001, Serial No. 996243 entitled Osteoimplant, Method of Making Same and Use of the Osteoimplant for the Treatment of Bone Defects filed Nov. 28, 2001 in the name of John Winterbottom et al., now U.S. Pat. No. 6,478,825 and Ser. No. 60/264,601 entitled Implant Insertion Tool filed Jan. 26, 2001 in the name of John M. Winterbottom et al. and corresponding to PCT application PCT/US01/44414 filed Nov. 6, 2001, all incorporated by reference herein.

U.S. Pat. No. 5,899,939 to Boyce et al. discloses a bone-derived implant made up of one or more layers of fully demineralized or partially demineralized cortical bone and optionally one or more layers of some other material. An adhesive, or other bonding techniques or mechanical fasteners such as pins, screws, dowels and so on or interengaging features may be used to connect the layers. The implants can be shaped by machining or press molding.

Surgical procedures using spinal implants for fusing adjacent vertebrae to treat various pathologies are well known. Implants for such procedures take a wide variety of shapes, forms and materials from bone to titanium inert materials, rigid and elastic, circular cylindrical, wedge shapes, cages with or without openings to accept bone fusion promoting material. The implants are dimensioned and shaped to provide a predetermined disc space between the fused adjacent vertebra.

Generally, bone growth promoting material is used in conjunction with the implant especially inert implants of metal, ceramic or other synthetic compositions. Often this growth promoting material is in the form of bone chips or bone fibers. The bone source may be the iliac crest of the patient which is not desirable due to pain and long recovery periods.

Implants of generally one kind of design are described in certain of the aforementioned copending applications.

Published PCT international applications WO 99/09914 and WO 00/24327 also disclose spinal intervertebral implants of different shapes and are incorporated by reference herein. Manufacturing processes and tools for insertion are also disclosed.

U.S. Pat. No. 4,878,915 to Brantigan illustrates a spinal intervertebral implant. The implant is circular cylindrical and has a threaded bore and two opposing radial slots at one end for receiving an insertion tool threaded stud and prongs.

U.S. Pat. No. 4,904,261 to Dove et al. illustrates an inert C-shaped spinal fusion implant.

U.S. Pat. No. 5,192,327 to Brantigan discloses a prosthetic implant for vertebrae.

U.S. Pat. No. 5,443,514 discloses a method for fusing adjacent vertebrae using a spinal implant. The implant has through openings to provide for blood flow and bone growth from one side of the implant to the other side of the implant to adjacent vertebra. The implant is made of chopped fiber reinforced molded polymer, stainless steel or titanium.

U.S. Pat. No. 5,522,899 to Michelson discloses spinal implants which are substantially hollow rectangular configurations. In one embodiment, a series of implants are placed side by side in the intervertabral space to substantially fill the disc space. Autogenous bone material is packed within the hollow portion to promote bone growth. In other embodiments a substantially rectangular member has a series of ridges on upper and lower surfaces. The material of the implants is not described.

U.S. Pat. No. 5,769,897 to Harle discloses a wedge implant having a first component of a synthetic bone material such as a bioceramic material and a second component of a synthetic bone material such as a bioceramic material or bone tissue or containing bone tissue in combination with other biointegration enhancing components. The second material is incorporated in accessible voids such as open cells, pores, bore, holes and/or of the first component. The first component forms a frame or matrix for the second component. The first component imparts strength to the second component. The first and second components can receive one or more pharmaceutical substances. The second component can fully or partially disintegrate upon completion of the implanting to promote penetration of freshly grown bone tissue into the first component.

U.S. Pat. No. 5,716,416 to Lin discloses an elastic intervertebral implant.

U.S. Pat. No. 5,741,253 to Michelson, discloses an implant that is tubular and cylindrical and is inserted in an opening in the spine formed by a drill.

U.S. Pat. No. 5,443,514 to Steffee discloses a spinal implant that is wedge shaped with two opposing flat parallel surfaces and two inclined surfaces which converge toward one end. The flat surfaces have recesses which receive the clamp of an insertion instrument.

U.S. Pat. No. 6,200,347 to Anderson et al. discloses a composite bone graft for implantation in a patient. The graft includes two or more bone portions and one or more biocompatible connectors which hold the bone portions together. Textured surfaces are provided. Disclosed are different embodiments and shapes.

U.S. Pat. No. 6,025,538 to Yaccarino discloses a composite allograft bone device comprising a first bone member body defining a face that includes a plurality of intersecting grooves cut into the face defining a plurality of spaced projections of a first pattern. A second bone member body has a face that includes a plurality of angularly spaced grooves forming projections in a second pattern on the first bone member body. The projections and grooves mate to form the composite body. An angled through bore is in the two bodies and includes a dowel mounted in the bore.

PCT application WO 99/09914 discloses a cortical bone cervical Smith-Robinson fusion Implant. Disclosed are different spinal implants of cortical bone and methodology for making. The implants are D-shaped or C-shaped and may be formed in layers which are pinned together. A cancellous plug or plug made of other biocompatible material with bone growth materials is used with the D-shaped implant.

Fred H. Albee in *Bone graft Surgery in Disease, Injury and Deformity*, D. Appleton-Century Company, NY., 1940, pages 20-22, discloses the fabrication of bone pegs and screws using a bone mill and in *Scientific American*, April 1936, Vol. No. 4, pages 178-181, discloses the formation of various bone configurations in a manner similar to woodworking methodology using similar tools as in woodworking. FIG. 3 thereof discloses various bone configurations fabricated in the manner disclosed. FIG. 4 shows a bone mill using various tools.

The present invention is a recognition of a need for improvements to the above described implants and related connecting structures as well as processing methodology for formation of such implants.

A spinal fusion implant for fusing together two adjacent vertebra according to an aspect of the present invention comprises a first member having first and second opposing sides and a first bore defining a central, longitudinal first axis, the first bore being in communication with at least the first side. A second member has third and fourth opposing sides and a second bore in communication with at least the third side, the second bore defining a second central longitudinal axis, the first and second axes forming a first pair. An elongated first pin is located in the first and second bores for securing the first member to the second member at the interface formed by the facing first and third respective sides, the pin having a first section defining a third central longitudinal axis and a second section defining a fourth central longitudinal axis, the third and fourth axes forming a second pair.

One axis of at least one of the first and second pair of axes is offset relative to the other axis of the at least one pair of axes so as to place the pin in relative compression and tension in the first and second bores for providing a compressive load on the surface of the first and second bores to frictionally secure the members together. The first and second members define a planar interface, further including an interengaging arrangement coupled to the first and second members adjacent to said interface for precluding translation displacement of the members transverse to said first and second axes in response to the compression load on the surface of the bores.

The first member has a planar interface surface at the first side, the second member having a planar interface surface at the third side for abutting the first member planar surface in a plane, the first member defining an edge, the second member having a leg extending therefrom, the leg for abutment with the edge to form said interengaging arrangement to preclude relative translation of the first and second members in at least one direction in the plane, the compression and tension creating compression forces in said members in the at least one direction. Each member is L-shaped with the leg of each member forming a recess with its planar interface surface, each member having a portion adjacent to its leg in the recess of the other member.

A spinal fusion implant according to a further aspect for fusing together two adjacent vertebra comprises a first member having first and second opposing sides and a first bore defining a central longitudinal first axis, the first bore being in communication with at least the first side. A second member has third and fourth opposing sides and a second bore in communication with at least the third side, the second bore defining a second central longitudinal axis, the first and second axes forming a first pair. An elongated first pin located in the first and second bores for securing the first member to the second member at the interface formed by the facing first and third respective sides, the pin having a first section defining a third central longitudinal axis and a second section defining a fourth central longitudinal axis, the third and fourth axes forming a second pair. One axis of at least one of the first and second pair of axes is offset relative to the other axis of the at least one pair of axes so as to place the pin in relative compression and tension in the first and second bores for providing a compressive load on the surface of the first and second bores to frictionally secure the members together; wherein the offset is formed by the at least one axis being non-parallel to said other axis.

In a further aspect, the one and other axes intersect.

A spinal fusion implant for fusing together two adjacent vertebra according to a still further aspect comprises a first member having first and second opposing sides and a first bore defining a central longitudinal first axis, the first bore being in communication with at least the first side. A second member has third and fourth opposing sides and a second bore in communication with at least the third side, the second bore defining a second central longitudinal axis, the first and second axes forming a first pair. An elongated first pin is located in the first and second bores for securing the first member to the second member at the interface formed by the facing first and third respective sides, the pin having a first section defining a third central longitudinal axis and a second section defining a fourth central longitudinal axis, the third and fourth axes forming a second pair. One axis of at least one of the first and second pair of axes is offset relative to the other axis of the at least one pair of axes so as to place the pin in relative compression and tension in the first and second bores for providing a compressive load on the surface of the first and second bores to frictionally secure the members together; wherein the first and second sections are curved forming said second pair of axes as a single continuous curved axis.

In a further aspect, the projection of the first and second elongated bores in a direction normal to said planes forms an X shaped image of said first and second elongated bores in a plane parallel to said parallel planes.

In a further aspect, there are two sets of said first and second bores and a second pin, the first pin engaged with the first set of bores and the second pin engaged with the second set of bores. Each set of bores are inclined at an angle not perpendicular to the plane of the interface of the members, the angle of one set of bores being oriented opposite to the orientation of the other set of bores.

In a still further aspect, the members each comprise sheet material, the sheet material having opposing surfaces defining said sides, the members forming a wedge having proximal and distal ends, the proximal end forming an anterior end and the distal end forming a posterior end, the implant having a longitudinal axis normal to the interface of said members and extending through said proximal and distal ends normal to the interface of said members, the elongated first pin extending along said longitudinal axis.

In a further aspect, a pair of first and second pins, a different pin being in each member bore for attaching the members to each other, the pins and bores being arranged to place the pins in both compression and tension, at least one of the bores having first and second sections each defining a first transverse dimension defining a corresponding pair of first and second respective central longitudinal axes. One axis of one of the pair of first and second axes being offset relative to the other axis of the pair of axes so as to form a first offset arrangement of a given orientation and to place the first pin in relative compression and tension in the at least one bore for providing a compressive load on the surface of the at least one bore to frictionally secure the members together.

A method of forming a bone implant according to an aspect of the present invention comprises assembling two cortical bone planks in parallel abutting relation, boring at least one first bore in one of the bone planks in a first direction, and boring at least one second bore in the other of the bone planks in a second direction generally opposite the first direction wherein the first and second bores are offset relative to each an amount such that a straight bone pin inserted in the bores is placed in compression and tension.

A method of forming an implant according to a further aspect comprises forming first and second cortical bone members with a bore in each member, contracting a cortical bone pin by dehydrating the pin, inserting the dehydrated pin in the bore of each member; and then expanding the inserted pin to create an interference fit between the pin and bone members in the bores.

A process for forming a bone implant according to a further aspect comprises forming a plurality of planks of cortical bone, the planks having a broad surface terminating at edges, the surface being defined by a length and a width, the planks each having a thickness, forming the broad surface of each of at least two of said planks for mating in abutting relation, surface demineralizing all surfaces of the at least two planks, clamping together the two at least planks with said mating broad surfaces abutting, washing the clamped at least two planks, forming at least one bore in the at least two clamped planks transversely the broad surfaces for receiving a locking pin therein, forming a locking pin and inserting the locking pin in said at least one bore in each of the at least two clamped planks, forming a plurality of ridges on first and second opposing sides of said clamped planks, surface demineralizing the formed ridges, freezing and/or drying under clamping pressure the resulting demineralized implant; and then unclamping the implant.

A process of making a spinal implant according to a further aspect comprises forming first and second hydrated cortical bone planks with aligned bores, surface demineralizing a bone pin and then dehydrating the pin, inserting the dehydrated pin into the aligned bores; and then swelling the demineralized pin surface to provide a friction fit between the pin and bores.

IN THE DRAWINGS

FIG. 1 is an isometric view of a spinal implant according to one aspect of the present invention;

FIG. 2 is a sectional plan view of the implant of FIG. 3 taken along lines 2-2;

FIG. 3 is a side elevation sectional view of the implant of FIG. 1;

FIG. 4a is a side elevation view of a locking pin useful for explaining certain principles of the present invention;

FIGS. 17-21 and 40-41 are respective side elevation views of locking pins according to further embodiments of the present invention;

FIGS. 22-26b, 27, 31 and 33 are isometric views of locking pins according to still further embodiments;

FIGS. 28 and 29 are plan views of locking pins of still further embodiments;

FIG. 30 is an isometric view of the pin of FIG. 13;

FIG. 32 is a plan view of a bore in an implant according to a further embodiment for receiving a locking pin;

FIGS. 68-70 are respective isometric, side elevation sectional and top plan views of a tool for fabricating several of the disclosed locking pins;

FIG. 71 is a side elevation view of an implant with a locking pin in a bore thereof for securing several bone planks together;

FIG. 72 is a side elevation sectional view of an implant according to a further embodiment useful for explaining certain principles of the present invention;

FIG. 73 is an isometric view of an implant with a groove cutting tool;

FIG. 74 is an isometric view of the implant of FIG. 73 after the grooves are formed in a surface thereof;

FIGS. 75-77 are isometric views of implants according to further embodiments;

FIG. 77a is a sectional side elevation view of the implant of FIG. 77;

Figure 4:
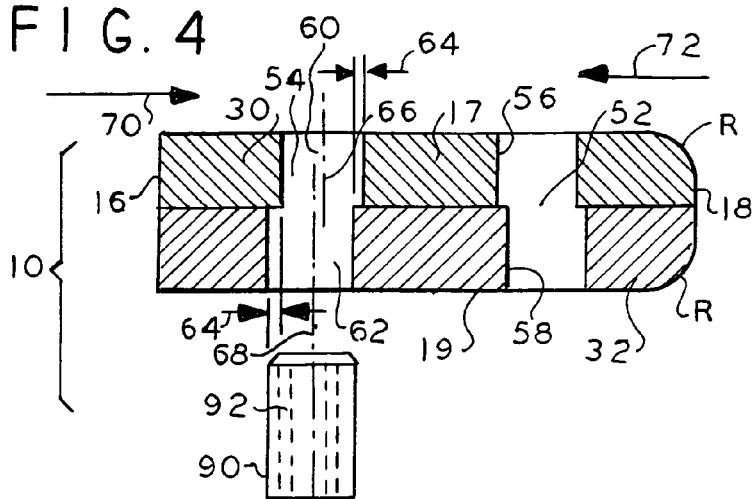
FIG. 4 is an exploded sectional plan view similar to the view of FIG. 2 with the locking pins prior to insertion.

The intervertebral wedge shaped implant 10, FIGS. 1-3, which is also referred to as a graft, is bone derived, preferably relatively hard cortical bone, and, in a further embodiment, may be formed generally as described in more detail in the aforementioned patent application Ser. No. 09/328,242 now U.S. Pat. No. 6,277,149, incorporated by reference herein. The implant, as well as the other implant embodiments described below, may also be fabricated as described in the aforementioned U.S. Pat. No. 5,899,939 incorporated by reference herein in its entirety. The implant 10 has a top surface 12, a bottom surface 14, two opposite end surfaces 16 and 18 and two opposing side surface 17 and 19. The surfaces 12 and 14 have ridges or saw teeth 20. The teeth 20 are formed by parallel grooves normal to the longitudinal axis 22 of the implant and extend completely across the surfaces 12 and 14. The teeth 20 have an inclined rake 24 facing end 18 and a rake 26 facing end 16. Rake 26 is normal to the axis 22 so that the teeth 20 bite into the vertebra to preclude migrating out of the disc space after insertion. The implant is inserted anterior end 18 first, which is higher dimension h than the posterior end 16. Thus the rake of the teeth preclude the implant from migrating out of the disc space opposite to the insertion direction. The angle of inclination of rake 24 may be about 45°. The grooves forming the teeth may be about 1 mm in depth for an implant having the dimensions set forth in the aforementioned copending application Ser. No. 09/328,242. These teeth form serrations in the form of repetitive identical saw teeth. The saw teeth have a pitch which is determined for a given implant configuration. The rake surfaces may be both inclined relative to the implant longitudinal axis 22. The teeth 43 serve to prevent withdrawal of the implant after insertion.

Surfaces 12 and 14 are preferably inclined to form a wedge shaped implant, sometimes referred as a ramp, but also may be rectangular of uniform thickness or curved as in a cylindrical dowel. Surfaces 12 and 14 of implant 10 converge at posterior end 16, to a height in the range of about 7 to 13 mm. The height increases toward the respective anterior end in the range of about 9 to 15 mm in one embodiment. Other shapes and configurations are described below herein in reference to others of the figures.

Surface 16 is planar and forms the posterior end and surface 18, which is formed rounded with two radii R, FIG. 1, and which forms the anterior end of the implant. Surfaces 12 and 14 each have a tapered or chamfered portion 28 at end 18 to facilitate insertion of the implant into a disc space to minimize trauma to the patient.

Preferably the implant is formed from cadaveric human or animal bone an/or bone composites of sufficient strength comparable to cortical bone to support adjacent vertebra when fused thereto, and more preferably of a long human or animal bone and comprising primarily cortical bone, which is hard and exhibits relatively good strength.

Figure 60:
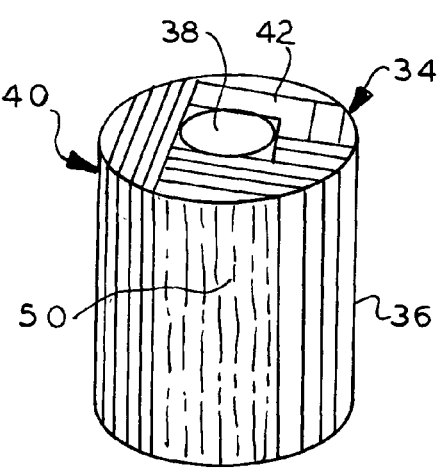
FIG. 60 illustrates an isometric view of a long bone used to fabricate the implant portion of FIG. 59 and bone planks used to form implants according to the various disclosed embodiments.
Figure 59:
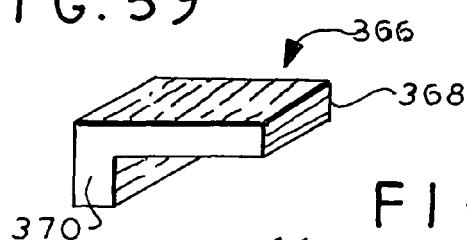
FIG. 59 illustrates an implant element which may be further processed to form the implants or portions thereof of FIGS. 42 and 43.

The implant 10 comprises two sheets or planks 30 and 32 of cortical bone. The term sheets as used herein and in the claims is intended to include planks, wafers and other relatively thin sheet-like material and as used herein is interchangeable with such other terms. Sheet material of different thicknesses and according to the relative shape are referred to as planks herein in the interest of illustration of a relatively long sheet with a narrower transverse dimension as common with conventional material known as planks. Preferably, the sheets or planks forming the implant 10 are formed from a cortical ring cut from a long bone, such as the fibula, ulna, humerus, tibia or femur by cutting the bone transversely across the diaphysis or metaphisis of the bone as shown in FIG. 60. This forms a cortical ring 36.

Figure 61:
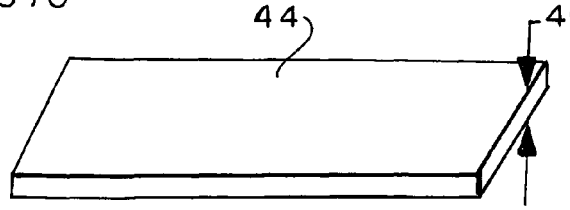
FIG. 61 is an isometric view of one of the bone planks of FIG. 60 after further processing.

In FIG. 60, long bone 34 is typically formed from larger bones to form implants for thoracic and lumbar spinal fusion. Smaller bones including the ulna, radius and fibula are used to form implants for cervical spinal fusion. The bone 34 is cut into a ring 36 having a central open core 38 formed by the medullary canal. The bone is cut into planks 40 which are elongated rectangular sections with opposing planar sides and parallel edges. An L-shaped member 42 may also be cut from the bone to form an implant structure as described later. The planks 40 are further processed to form a finished plank. The cut bone is secured and the edges machined to provide, in one embodiment, a substantially rectangular plank with squared edges as shown by implant plank 44, FIG. 61.

Figure 87:
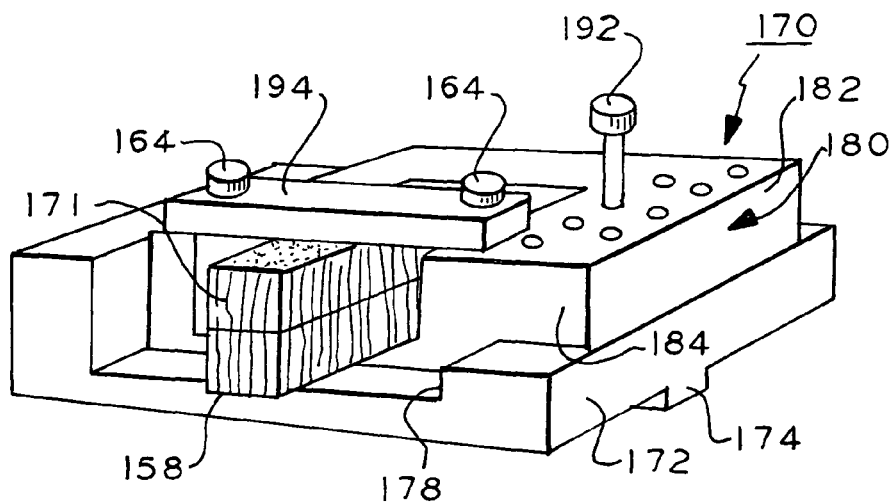
FIG. 87 is an isometric view of a tool useful for shaving a portion off of an end of an implant.
Figure 88:
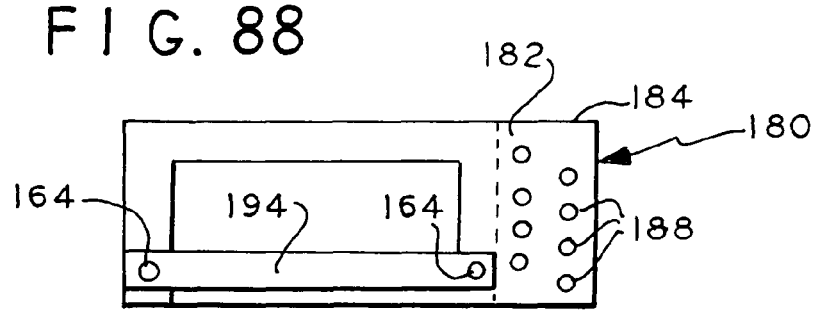
FIGS. 88 and 89 are plan views of different portions of the tool of FIG. 87.
Figure 89:
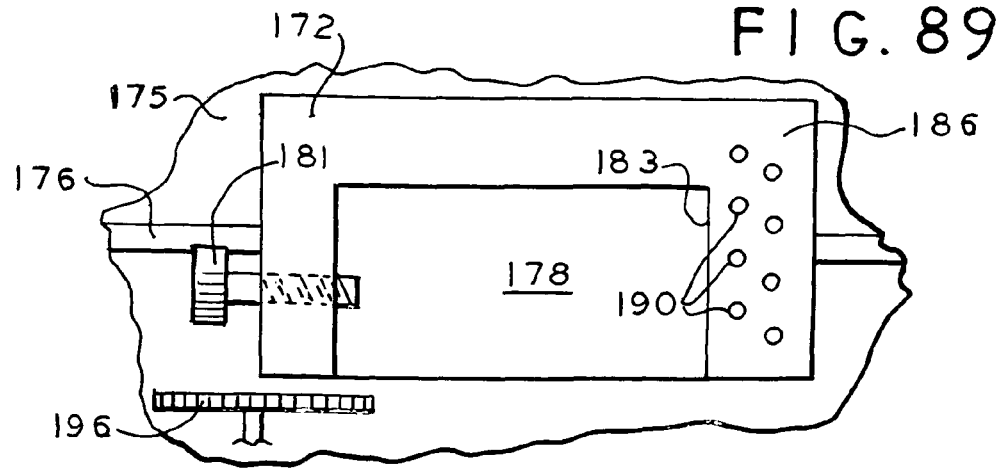

In the alternative, the planks may be formed as followed. In FIGS. 87-89, a clamp assembly 170 clamps a bone 158, cut from a donor long bone, to form end 171 into a plank. Clamp 170 comprises a base 172 having a rib 174. Rib 174 slides in guide slot 176 (FIG. 89) of a saw table 175. The base 172 has a rectangular recess 178 for receiving a complementary shaped clamp 180. Clamp 180 has a rectangular body 182. Body 182 has a flange section 184 overlying section 186 of the base 172. Alignment apertures 188 are used to align clamp 180 to the base 172 alignment apertures 190. Alignment pin 192 is inserted in apertures 188 and 190 to align the clamp 180 to the base 172 at the desired position.

A clamp bar 194 is screwed to body 184 by screws 164 to clamp the bone 158 to the clamp 180. The clamp 180 is secured by screw 181 to base 172. This clamp 170 forms a fixture that permits incremental cutting of the bone 158 into planks with 0.5 mm increments depending upon the hole combination of apertures 188 and 190 set by pin 192. The clamped bone 158 when attached to the base 172 permits the overhanging end 171 to be sliced by saw blade 196 of table 175. The bone may be adjusted in position by resetting the pin 192 in different apertures in the clamp. Employing this technique bone planks may be formed. This arrangement allows easy adjustment of the clamp 180 position relative to the saw blade 196. Large easily seen markings (not shown) on the clamp components and the large pin 192 permits ease of adjustment. The claim 170 is precisely positioned in the slide slot 176 which aligns the clamp 170 and clamp 180 via the slide rib 174 in the slot 176. Once the clamp screw 181 is tightened, the clamp 180 is positioned against the wall 183 of the base 180 forming recess 178. This prevents angular displacement of the clamp 180 and provides accurate alignment of the clamp 180 to the blade 196. The above techniques are given by way of example. Other known fabrication techniques may be used to accurately machine the implant body to the desired dimensions.

The planks 40 may be in a range of less than 1 mm to in excess of 20 mm thick. Preferably the planks 30 and 32, FIG. 1, of implant 10 have a thickness 46 of about 10-20 mm each to form a composite two plank thickness 48 of about 20-40 mm. The planks have a length defined by ends 16 and 18 of about 20-30 mm and preferably 23-26 mm. The anterior end 18 height h of the implant 10 may be about 7-18 mm and preferably 9-15 mm. The posterior end 16 may have a height of about 5-15 mm and preferably about 7-13 mm. The width may be about 7.8 to 8.8 mm. The opposing sides 12, 14 of the implant in contact with adjacent vertebrae in the posterior to anterior direction, as determined by the site of the implant in the patient, may taper at an angle of about 5 degrees. These dimensions are formed in the implant 10 after the planks are attached to each other.

In FIG. 2, two planks 30 and 32 which may be identical, may also be bonded together at their broad surfaces which mate in complementary fashion. Such bonding is disclosed in U.S. Pat. No. 5,899,939 discussed in the introductory portion. In the present embodiment the broad surfaces are planar, but in other embodiments these mating surfaces may have interlocking surface features such as projections and grooves, e.g., dove tail joints and mortise and tendon joints and the like as described below in more detail. Preferably the mating surfaces are partially demineralized to assist in bonding these surfaces together. In addition, adhesives, as described in the aforementioned U.S. Pat. No. 5,899,939 may be preferably employed.

Figure 80:
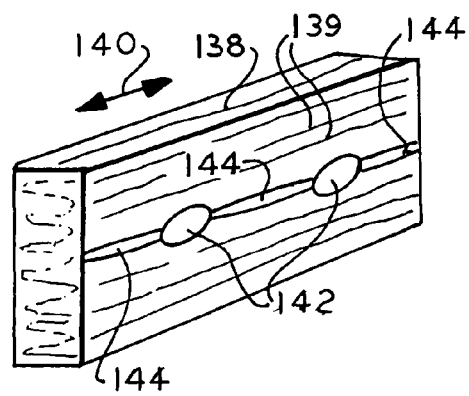
Figure 82:
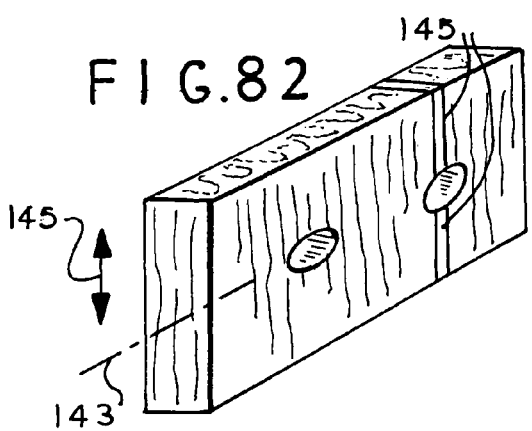

Prior art approaches to securing multiple planks together relied on different diameters between locking pins and the bores in the planks in which the pins are inserted. This difference in diameters is employed to create an interference fit between a locking pin and the plank bores. For example, U.S. Pat. Nos. 6,200,347 and 6,025,538 disclose for example press or interference fit of pins into mating bores in the graft formed of multiple layers. The disadvantage of this approach is that when the implant is dried, the hole size relative to the pin may lead to splitting of the bone planks as shown in FIGS. 80 and 82. In addition, the planks may become loose and may no longer be affixed by the pins. When the interference is reduced to prevent splitting, the holding power of the pins is reduced. Thus the interference arrangement is unsatisfactory.

In FIG. 80, a plank 138 is shown with its fibers 139 running in directions 140. If two pins 142 were inserted into corresponding bores in the plank 138 in interference fit, the compressive and shear loads from the pins would cooperate reinforcing each other to cause the plank to split at splits 144 which tend to separate the plank into two longitudinal pieces. However, if the fiber directions 145 are normal to the plank longitudinal axis 143 instead of parallel, as shown in FIG. 82, the splits 145 caused by pins 146 are normal to the axis 143 and do not cooperate with splits caused by other pins. This latter action is more preferable than that of FIG. 80 as the magnitude and tendency to split is reduced. Therefore, the fiber directions of the planks is preferably normal to the longitudinal axis 22 of the implant.

Two bores 52 and 54, FIG. 4, are formed in the composite blank formed by planks 30 and 32. The term "bore" as used herein does not imply that the bore is a through bore or that all portions of the bore are identical. In this embodiment, the bores 52 and 54 have different bore sections wherein only a portion of the sections are in communication with each other and other portions have stepped surfaces. Bores 52 and 54 are mirror images of each other and are oriented approximately 180° relative to each other in the two planks 30 and 32. Bore 52 comprises a subset of offset bores 56 and 58 whose central axes are offset in the longitudinal direction of the implant axis 22. Bore 54 comprises a subset of offset bores 60 and 62 whose central axes are also offset in the longitudinal direction of the implant axis 22. Subset bore 56 is preferably identical to subset bore 60 in diameter and subset bore 58 is preferable identical to subset bore 62 in diameter and, more preferably, all of the subset bores 56, 58 60 and 62 are identical in diameter.

The subset bores 60 and 62 are offset distance 64 and the subset bores 56 and 58 are also offset the same distance 64. Bore 60 has an axis 66 and bore 62 has an axis 68 with the axes offset from each other by distance 64. Similarly, the axes of subset bores 56 and 58 are offset from each other, but in an opposite direction as the direction of offset of the subset bores 60 and 62.

Thus bore 60 is displaced from bore 62 in direction 70 of the implant longitudinal axis 22 and bore 56 is axially displaced on axis 22 from bore 58 in direction 72 opposite to direction 70. Preferably the offset distance 64 is about 0.1 to 1 mm for a bore 52 or bore 54 diameter of 3-5 mm, the subset bores each being circular cylindrical. This offset range value may differ in accordance with a given implementation and the strength and fiber characteristics of the particular bone being used. Thus the offset distance 64 of each of the respective bores 56 and 60 in plate 30 is in a direction toward each other relative to the axes of the corresponding subset bores 58 and 62. This relative direction of the offset is important.

Figure 83:
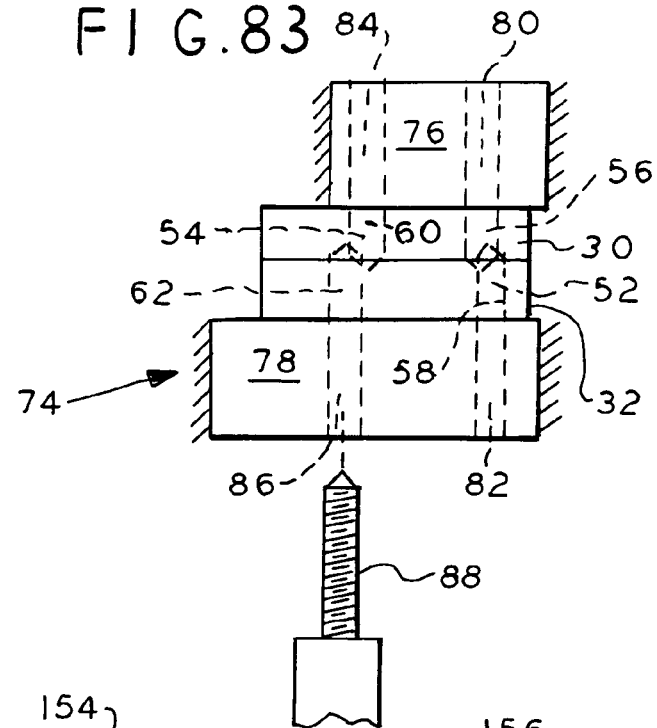
FIG. 83 is a side elevation view of a tool useful for creating certain bores in a representative embodiment of an implant.

In FIG. 83, the bores 52 and 54 are formed by tool 74. Tool 74 comprises an upper tool steel guide 76 and a lower tool steel guide 78. The guides 76 and 78 include locating pins (not shown) for aligning guide holes 80, 82, 84, and 86 relative to each other to produce the bores 52 and 54. The guides 76 and 78 are clamped together by a clamp not shown in this figure.

Guide holes 80 and 82 receive drill bit 88 of a drill for drilling the respective bores 56 and 58 and the guide holes serve to guide the bit 88 to form respective bores 60 and 62. The tool 74 may be used to form bores in the various implant embodiments described hereinafter with minor modifications to accept the different implant and bore configurations. This arrangement provides precision bore locations in the implant. The tapered tip of the drill bit chamfers the edge of the bores in the adjacent planks. This chamfering permits ease of passage of an offset pin from one bore to the other in the adjacent planks. After drilling the bores, the pins can be pressed into place without disturbing the clamped guides 76 and 78.

In FIG. 4, a right circular cylindrical bone pin 90 by way of example and which could also be tapered is inserted into each bore 52 and 54. The pin 90 has a diameter that is substantially the same as that of the bores 52 and 54 so that there is no press or interference fit between the pin and bores. The pin 90 is cortical bone and its fibers 92 run generally along the pin longitudinal axis 94. This direction of the fibers gives the pin 90 maximum shear strength in the transverse direction to resist shearing of different sections of the pin in the presence of shear forces medially the pin along its axis 94 due to the offset of the subset bores in which it is inserted. The pin 90 preferably by way of example may have a diameter in the range of about 2 to 5 mm according to the dimensions of the implant involved and the corresponding bore sizes. Other diameters of the pins may be used according to a given implementation.

Figure 85:
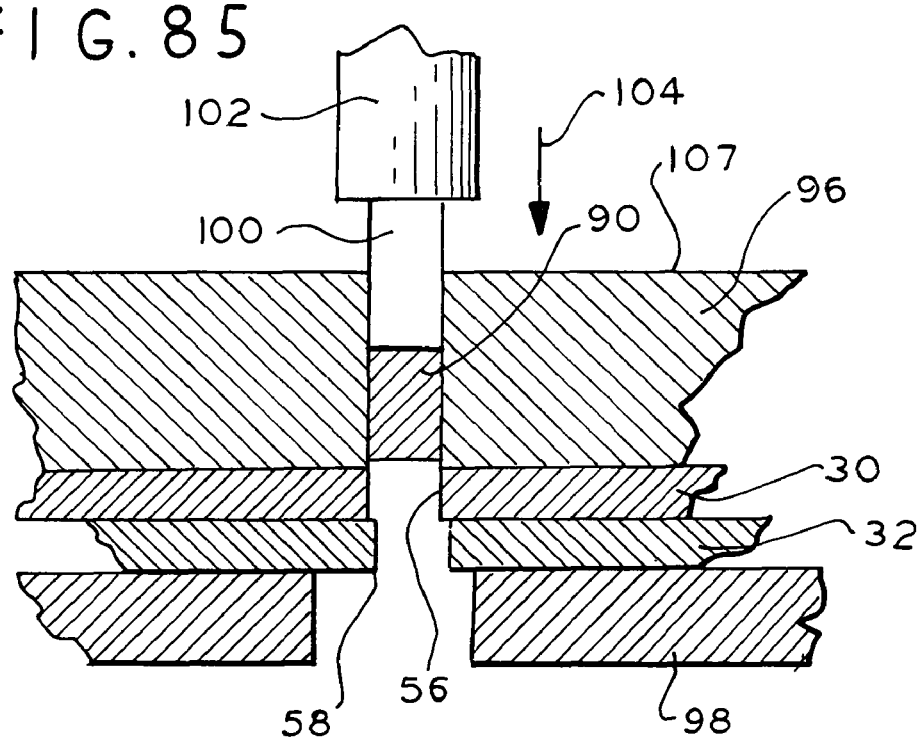
FIGS. 85 and 86 are side elevation sectional views of a tool for inserting pins into the bores in an implant.

A pin 90 is forced into each bore 54 and 52. In FIG. 85, planks 30 and 32 are clamped between two dies 96 and 98. A plunger 100 on tool 102 mates in a corresponding bore of the die 96 and is forced in direction 104 against the pin 90 by an operator mechanism (not shown) such as a threaded or hydraulic drive. The pin 90 is then forced into the subset of bores 56 and 58 of respective planks 30 and 32. The pin 90 end surfaces, when the pin is fully inserted, are flush and coextensive with the outer side surfaces of the implant comprising the two joined planks 30 and 32.

Figure 86:
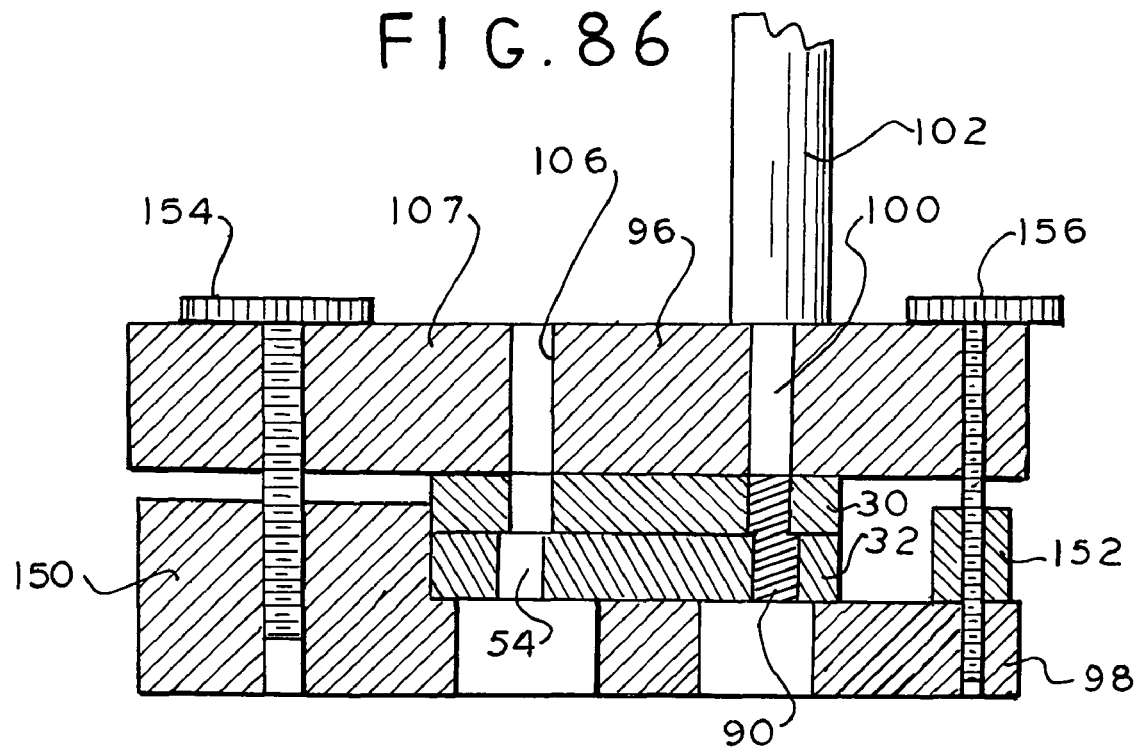

In FIG. 86, the pin 90 is shown fully inserted. After insertion, the tool 102 is used to insert a second pin 90 (not shown) into the other bore 54 similarly via tool guide hole 106.

In FIG. 4a, pin 90 is a right circular cylinder and has two opposing end surfaces 91 and 93 which are flat and normal to the longitudinal axis 94. As mentioned the cortical bone fibers have a direction generally parallel to the axis 94. The end surfaces 91 and 93 after insertion of the pin 90 into the bore 52 or bore 54 are flush with the sides of the 17 and 19 of the implant 10 as also mentioned above. As shown in the figure the pins 90 appear bent. However, in practice this bending is exaggerated as the offset value 64, FIG. 4, is relatively small.

When the pin 90 is forced into the bore 52 or 54, it bends somewhat in response to the offset axes of the bore sections 60, 62 or 56, 58 of the two bores 52 and 54. The bend occurs generally at the interface between the two planks 30 and 32 at which the offset between the two bores is first reached by the pin upon insertion. In FIG. 4a, the pin 90 is thus bent as manifested in principle by the dashed lines 106 and 108 which are shown merely for purposes of illustration as the pin in practice is bent as shown in FIG. 2.

The bending of the pin 90 creates both latent compression and tensile forces in the pin as known from general strength of materials principles relating to bent beams. If the pin 90 is assumed to be bent in the direction of the dashed lines 106 and 108 for purposes of discussion, then the region of the pin to the left of the axis 94 in the figure will be in compression as shown by arrows 110. The region to the right of the axis 94 will be in tension as shown by arrows 112. The compression and tension create latent compressive and tensile potential energy resilient forces in the pin and also place the pin in shear. These forces act in a direction to straighten the pin to its original configuration as shown in FIGS. 4, 4a and 17.

In respect of pin fabrication, bones are anisotropic, i.e., strength varies according to direction due to the fibrous structure. To maximize pin strength, the fiber direction is in the axial length direction of the pin. In this way transverse shearing forces must break the fibers, FIGS. 79 and 81. If the force is in the direction of the fibers, the fibers can separate as shown in FIGS. 80, 82. The pins may be made of bone such as the ulna and radii or left over scraps from bone used to make the implant planks.

The larger the pin diameter, the greater its holding power. The surface area of a pin increases with its diameter, i.e., $A = \pi d L$ where A is the surface area, d is the diameter and L is the length of the pin. Thus doubling the pin diameter also doubles the surface area. Since in the offset pin arrangements, the compression loads induced on the adjacent implant surfaces is utilized to create static friction forces, the greater the surface area the greater the friction load for a given force. Therefore, the pins should be as great a diameter as possible for a given implant configuration. This can be determined empirically for each implant design.

Hole saws are preferable for generating pins, Pins using such saws were fabricated with diameters as small as 1.5 mm. Hand held saws as well as machine operated saws may be used according to the saw design. Since bone is relatively elastic, extremely high precision in making the pins is not required. In such cases, once the pins are formed no other machining of the exterior outer surface is required other than cutting the pins to length. In contrast, metal pins require a much greater degree of accuracy to obtain a given fit in a bore. Centerless grinding may be used to increase pin diameter tolerances. Such a process is especially useful for fabricating tapered pins. Because of the elasticity of bone, obtaining a friction fit can be achieved without extremely tight tolerances.

Pin bores are formed by drills which are available in all desired sizes and will complement the various pin diameters formed by hole saws. Such bores may also be finished with reamers if desired. Pins made of bone are axially strong in compression. However, the pins are relatively weak in bending and in radial expansion. These deficiencies can be overcome by inserting the pins through tubes or holes that provide radial support to the pins so that the pins can not expand radially outwardly under insertion loads, FIGS. 85 and 86. The guide holes should be longer than the pins and the pins are driven by closely matched plungers such as plunger 100. The plunger has a shoulder to limit the depth of insertion contacting the surface above the guide hole such as surface 107, FIGS. 85 and 86. The pin insertion depth may be any desired value with the pin flush or recessed into the implant bore or extending somewhat above the implant surface.

In general bone has spring back. This means the ID of a hole is slightly smaller than the corresponding drill size. The bone pins might fit easily into the drill guides but manifest a tight press fit in the bored holes. The bore size can be determined empirically by one of ordinary skill in this art according to various pin sizes being used, the texture and hardness of the pins and relative pin diameters and pin configurations. A drill guide may have a flared out top to allow easy bone pin insertion and a taper near the bottom to reduce the guide diameter to precisely the diameter of the hole in the implant.

Tapered pins which mate with tapered bores with shallow angles, e.g., less than about 10 degrees, are self locking. Forming a tapered bore is simple using a custom drill or reamer. A tapered pin is formed after the cylindrical pin is formed. Pins may be left unfinished after formation or may be sanded or ground to provide a smooth exterior to integrate the pin surface with the implant bore surface.

In FIG. 2, pin 90 on the left hand side of the implant generates a compressive force component in direction 114 in plank 30 and an equal compressive force component in direction 116 in plank 32, which forces are components of the latent compressive and tensile bending forces of the pin in the direction of the plane of the plank normal to the pin axis. These forces lock the planks 30 and 32 in their abutting relation precluding their separation. However, these forces do not tend to split the planks at the bores since the compressive forces are applied by the pin in only one direction in each plank. In contrast, an interference fit applies forces at the bore in opposite directions in the plank. These opposing forces tend to split the plank at the bore as discussed above. In the offset arrangement there are no opposing forces on the plank which would tend to separate the plank in the fiber direction at the bore.

Normally, without other restraining structure, the forces in directions 114 and 116 would merely slide the planks 30 and 32 relative to each other in these directions until the pin 90 is straight. Thus, a restraint is necessary to oppose the thrust from the misaligned bores-pins. This is to keep the planks in place resisting the opposing thrust forces in these directions. This restraint can take the form of a number of different embodiments. The basic construction principle of misaligned bores is effective no matter the orientation of the pins, parallel or angled to each other. The advantage is that holding power can be satisfactory with little or no diametrical interference between the pin and hole which greatly reduces the chances of splitting the planks.

In the present embodiment of FIG. 2, the above described restraint is in the form of a second pin 90 in the right hand side of the implant 10 drawing figure. This second pin 90 is inserted into offset bores 56, 58 (FIG. 4) which are offset to the same degree as bores 60 and 62 but in opposite directions to the offset of bores 60 and 62. That is, the offset of bore 58 relative to bore 56 is to the right in the drawing figure, direction 70, whereas the offset of bore 62 relative to the bore 60 is to the left, direction 72. Consequently the pin 90 in bore 52 is bent the same amount as the pin 90 in bore 54 but in the opposite direction along axis 22 (FIG. 3). Therefore, the compression forces in the planks 30 and 32 created by the right hand pin 90 are equal and opposite in directions 114 and 116, FIG. 2, to the directions of the forces created by the left hand pin 90. The forces of the two pins thus counteract each other and prevent the planks from moving in the axial direction, directions 70 and 72, FIG. 4. The resulting compressive loads on the planks 30 and 32 by the two pins frictionally locks the pins to the planks and thus locks the two planks together in a direction normal to the axis 22.

The pin fibers have a fiber direction generally normal to axis 22 and present a maximum resistance to shearing of the pins by the shearing forces in directions 114 and 116. These shearing forces are created by the compression loads on the planks at the offset plane. By offsetting the bores receiving both pins 90, a maximum locking action of the two planks in a direction normal to axis 22 is provided. It should be understood that the two planks are by way of example and any number of pins may lock together any number of planks as described herein. However, both pins need not be bent or inserted in offset bores. Only one such pin need be bent and the other pin may be inserted in a straight through bore (not shown in this embodiment) and held in place by a typical interference fit and/or bonding, for example. The other pin may be held in place by such friction interference fit, an adhesive or other securing arrangements.

This other pin prevents the axial displacement of the planks along the implant longitudinal axis 22 (FIG. 2). Still other arrangements may be provided to preclude relative axial displacement of the two planks 30 and 32 in response to the opposing compressive loads presented by one or more bent pins 90 in a corresponding offset bore.

In the alternative, friction fit of pins may be obtained by swelling of bone from hydration. This process requires the cutting of the pins and dehydrating them. The dehydration may use any process such as a vacuum, air drying and/or freeze drying, or any other desirable process. The dried pins are placed in normal (hydrated bone) bone, then the pinned implant is immersed in saline to hydrate and swell the pins. Thereafter, the pins will match the hydration state of the mating bone and the friction load should remain through freezing, freeze drying, rehydration and so on of the pinned implant. Rehydration of the pins can crack the surrounding bone if care is not taken. Therefore, relative dimensions of the pin and bores need be carefully matched. Once the pin is attached in this way, variations in the environment including temperature and humidity will affect the pins and implant uniformly so that both contract and expand in unison retaining the friction fit.

Figure 79:
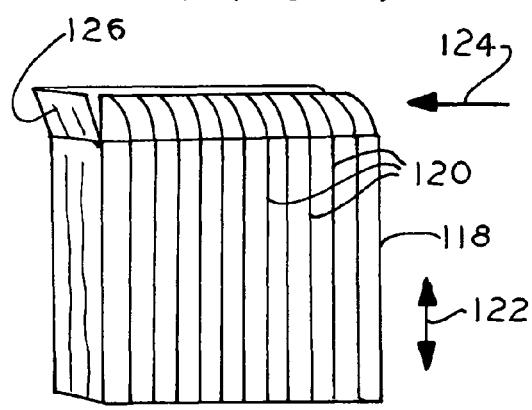
FIGS. 79-82 are isometric views of a cortical bone plank useful for explaining certain principles.
Figure 81:
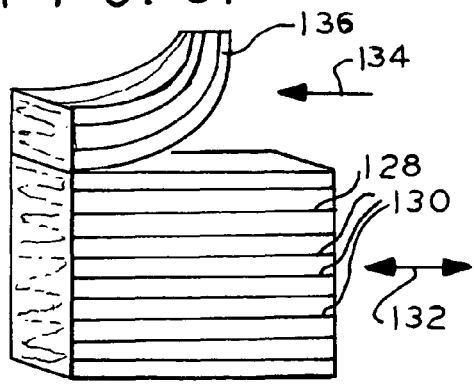

Another consideration in maximizing the strength of the implant 10 is to optimize the strength of the planks 30 and 32 in the presence of the compressive forces presented by the bent pins 90. In FIG. 79, a plank 118 has fibers 120 which have a fiber direction 122. If a shearing force 124 is presented normal to the fiber direction 122, the fiber portions 126 will merely bend in the direction of the force 124 rather than shear, as shown. In FIG. 81, however, in plank 128, the fibers 130 run in directions 132. In this situation, a shearing force 134 will separate the plank portion 136, separating it at the location of the shear force 134. Therefore, shearing forces where applicable are created normal to the fiber direction when possible.

Thus while two offset pins-mating bores are shown in FIG. 2, only one of such pins-bores needs to be so offset. The two offset pins-bores of course provide additional holding power to hold the two planks together and is preferred.

The implant 10 side walls 17 and 19 and top and bottom surfaces 12 and 14 are machined to form configurations such as the preferred taper, radii and saw teeth ridges of the implant 10, or left in their natural peripheral configuration (not shown). Other shapes as disclosed later herein may also be provided as desired. The angle of the wedge surfaces 12 and 14, FIG. 3, are arranged to accommodate the inclination of the adjacent vertebra to maintain the natural curvature of the spine. The various dimensions of the implant are disclosed in the aforementioned copending applications and patents incorporated by reference herein.

Surface demineralization reduces surface hardness and so can reduce precision needed in pin and hole machining. A problem is that the grain of the bone runs parallel to the axis of the pin and thus demineralized surface layers on the pin can be sheared off relatively easily, FIG. 81. Another problem is that the flexibility of demineralized surfaces means that micromovement of bone layers relative to one another under load can only be poorly constrained by demineralized pins. This leads to lower fatigue strength for the implant assembly. The more the demineralized layer on the pins is compressed, the more effective as a load transmitting surface. A practical way of achieving surface compression is to insert dehydrated, surface demineralized pins into a hydrated bone.

When the pin is dried after surface demineralization, it will shrink significantly, and especially at the demineralized layer. The dry pin can be inserted as a loose press fit such that the demineralized layer is not damaged by the insertion. Upon rehydration, the demineralized layer will swell, providing a tight fit in the bone planks. Any other use of demineralized pins is not preferred. Thus inserting dry pins with a light press fit results in the demineralized layer not being sheared off during the insertion of the pins.

Instead of or in conjunction with such surface demineralization of the pins, the bores in the implant receiving the pins can also be surface demineralized. Demineralization generally weakens the bone fibers. When the fibers in the bores run perpendicular to the bores, there is less possibility of shearing of the demineralized surface in the bores than on the pins. Furthermore, by demineralizing the bores, the load bearing diameter of the pins will not be reduced as might occur when the pins are surface demineralized. Therefore, it is preferable to use surface demineralized bores with undemineralized pins. However, surface demineralized pins may be used with surface demineralized mating bores if desired.

The planks with surface demineralized bores preferably have the bores formed somewhat undersized with respect to the pins so that the surface demineralized layers will be compressed upon pin insertion. Drying the planks before pin insertion after the bores are formed is not preferred because this leads to shrinkage of the bore diameters. Thus, the pins may be inserted after their being dried to provide the desired fit, but may be inserted without such drying.

Figure 84:
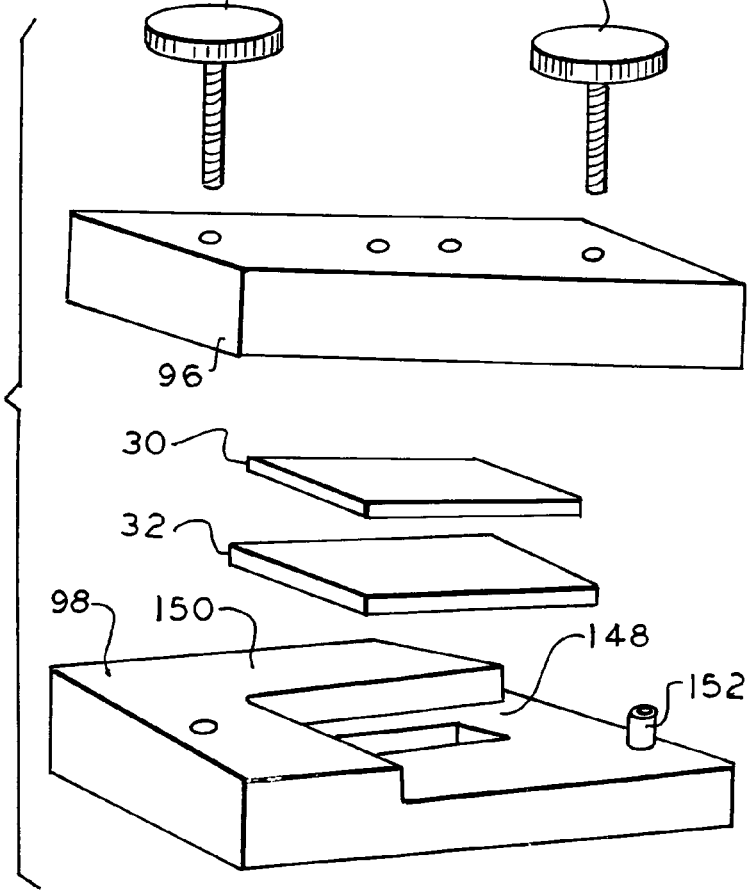
FIG. 84 is an isometric exploded view of a tool for processing an implant according to certain of the disclosed embodiments.

To surface demineralize the bores in the planks, the entire plank is surface demineralized after the plank bores are formed. The planks may be demineralized while assembled in the bore forming fixture such as illustrated in FIGS. 83 and 84. Reference is made to commonly owned U.S. Pat. Nos. 5,899,939, 6,123,731, 5,314,476, 5,507,813 and 5,298,254 for additional processes for making bone implants and related structures and incorporated by reference herein.

The planks may also be secured by adhesives with or without pins, screws or other mechanical fastening arrangements including interlocking projections and recesses and so on. Bone may be treated to make it adhesive without the use of an additional adhesive substance. See the aforementioned U.S. Pat. No. 5,899,939. Such treatment can include preparing a demineralized collagen layer adhesive or recrystallizing the demineralized surfaces to form interlocking crystals. Adhesives as a separate substance can also be employed.

In collagen bonding, the surfaces to be bonded are demineralized. A combination of heat and pressure produces the desired bond of the abutting demineralized surfaces. The exact mechanism for such bonds is not understood, but such bonds appear to be relatively weak. It is believed that strength may be imparted to the bonded joint by adding an ingredient that improves collagen solubility such as a salt. Further, the effect on inductivity by increasing collagen solubility is not known. Also, the ability of such bonds to withstand immersion in body fluids is also not known. It is believed better to bond bone fiber ends with a collagen bond rather than the collagen fibers parallel to the surface being bonded.

In recrystallization bonding, bone surfaces are painted with acid which promotes strong bond formation at least while the bone is dry. Such a bond dissolves in the presence of saline. It is known to use calcium phosphate self setting cements. Such cements may be used for such recrystallization bonding. Such cements are stable in body fluids. In one example, a cement system employs hydroxylapatite and phosphoric acid. The bone contains hydroxylapatite as its mineral base, and painting the surfaces with phosphoric acid forms a stronger bond than when the surfaces are painted with hydrochloric acid, forming a calcium phosphate cement.

Recrystallization bonding may be used to strengthen the implant of multiple bone planks for insertion into the disc space, for example, when the implant planks are not rehydrated. This provides an advantage over collagen bonding in that there is little or no demineralized layer present at the bond once the recrystallization effect dissipates. Thus the implant will exhibit greater strength than one with an internal collagen bond layer.

Recrystallization can be carried out by soaking or painting the bone surfaces with any acid, phosphoric acid being preferred. The wet surfaces are then joined. Bonding is enhanced by pressing the surfaces together under pressure and then drying the implant under pressure. The bonding process can also be used to bond a pin to an implant in the implant bore.

Total demineralization of one or more pin segments may also be useful. These segments are flexible due to the demineralization and may stretch under tensile load. During insertion, the pins are pulled in place so the demineralized segment stretches and, in response, shrinks in diameter. After insertion, the tensile force is removed, the pin relaxes and the demineralized segment returns to its normal configuration increasing in diameter locking the pin in place in interference fit with the mating bore.

Acid for adhesion of bone elements whether pins to the planks or planks to each other can be applied after assembly and delivered to the contacting surfaces by capillary action. Therefore, the acid need not be applied prior to assembly to obtain an adhesive bond.

In a variation of the acid treatment process described above, the bone planks can be assembled into an implant, and the assembled implant is then subjected to an acid treatment as discussed. The acid diffuses between the contacting bone surfaces. This effects the required amount of dissolution especially if the clamping pressure is minimized while the diffusion is in process. This process may be used in conjunction with the disclosed processes in the aforementioned U.S. Pat. No. 6,123,731 incorporated by reference herein.

If the implant with multiple planks is dried rather than stored frozen, warpage can be a problem. Normally implants made from bone do not warp or change dimensions when frozen. The warpage can cause cracks to appear between the bone planks. To resolve this problem, different approaches may be used individually or in combination. These approaches include minimizing the shrinkage, or constraining the implant so that warpage does not occur, or causing the planks to adhere so they cannot separate.

By removing most of the moisture by drying the implant at a temperature above freezing reduces shrinkage significantly, compared to freeze drying where the implant is frozen during most of the water removal process. After drying the implant at a temperature above freezing, remaining residual moisture may be removed by conventional freeze-drying, without introducing any additional shrinkage. In the alternative, glycerol may be introduced into the bone to reduce shrinkage prior to freezing and may also be used to assist in swelling the implant.

Physical restraint by clamping the implant during drying reduces the tendency to warp. Physical restraint is also beneficial in retaining the dimensions of the implant. For example, a threaded pilot hole for an insertion instrument can shrink during drying to the point where it is difficult or impossible for the inserter threads to engage the implant. A rigid screw placed in the hole before drying minimizes this problem.

The efficacy of the adhesion process can be enhanced if the bone assembly is clamped together and dried above freezing before a freeze drying step is carried out. The clamp can be retained or removed during a subsequent freeze dry cycle but retention is preferred.

To optimize support of spinal loads on the implant, it is preferred that the implant bone fibers run parallel to the spinal column. This is shown by the fibers 50, FIG. 1. However, since the spinal bone in contact with the implant is relatively softer, this fiber orientation may not be necessary and it may be advantageous to have the fibers parallel to the vertebra to optimize the strength of the implant during insertion into the disc space. In this regard, it is preferred that the planks be formed from the bone in the length direction of the bone, FIG. 60. In this way the fibers will run along the length dimension of the implant in the implant insertion direction. However, the problem with this fiber orientation is that if the load bearing surfaces are demineralized, there is the chance the demineralized surface might be scraped off of the implant during insertion due to its weakness. See FIGS. 79 and 81 in this regard.

The process for forming the implant such as implant 10 is as follows. The implant is formed from planks formed from a long bone as described in connection with FIGS. 60 and 61. The planks are then cut to the desired length and width of the implant, e.g., 0.5 to 20 mm thick. The various surfaces of the planks are then machined as applicable to form the plank 44, FIG. 61. The planks are then partially surfaced demineralized by dipping into a 0.6 normal HCL solution for a predetermined time period corresponding to the desired depth of demineralization. Only the outer surface portions of the bone will be demineralized. The strength imparting interior portions of the planks will not be compromised. Moreover, the bone may be treated using a variety of bone healing enhancing technologies. For example, bone growth factors may be infused into the natural porosity of the bone and/or the bone may be infused with acid to further demineralize the internal matrix of the bone where desired. These treatments may be performed using the pressure flow system disclosed in U.S. Pat. No. 5,846,484 incorporated by reference herein. While human bones are preferred, non-human animal bones may also be used.

The two planks 30 and 32 are then pressed together by a clamp as illustrated in FIGS. 83-86. In FIG. 84, planks 30 and 32 are placed between two clamp dies 96 and 98. The planks are placed in recess 148 formed by raised L-shaped portion 150 of the die 96 as best seen in FIG. 86. The die 96 abuts the portion 150 and stud 152. Two screws 154, 156 clamp the planks between the dies, FIG. 86. The bores in the planks are then formed as explained in respect of FIG. 83. In FIG. 83, the guides 76 and 78 represent the clamp dies 96 and 98, FIG. 84-86. The pins 90 are then formed and surface demineralized. The pins are formed from the long bone with the fibers oriented as discussed above.

The planks are transferred to a further clamp (not shown) so that the serration teeth may be formed. In FIG. 73, the clamped body 158 forming the implant is placed adjacent a rotating cutter 160 which cuts the teeth 164 into the body. As the teeth 164 are being formed the body 158 is translated in direction 161 to form elongated teeth. The opposite side 162 of the body 158 is then formed with the identical teeth 164 after the teeth are formed on one side, FIG. 74. In FIG. 74 the teeth 164 are different than teeth 20 to show a different configuration. Here the teeth 164 are formed as spaced V-shaped grooves in the body surface. One side of the groove is inclined at 45 degrees to the longitudinal axis and the other side is normal to the axis. The inclined side is on the posterior end 166 side of the grooves and the normal side of the grooves is on the anterior end 168 side of the grooves to provide biting into the mating vertebra in an implant withdrawal direction from the inserted position.

The bores 170, FIG. 74, for the locking pins are then formed in the body 158 after both sides of the body 158 are grooved. The body 158 after such machining is then surfaced demineralized. The surface demineralization of the bores is advantageous in that the fibers in the bores run perpendicular to the bore. There is thus much less chance of shearing the demineralized surfaces in the holes than on the pins. Also, demineralization of the bores means that the load bearing diameter of the pins will not be reduced as might occur when the pins are surface demineralized. It is preferable to use surface demineralized bores with undersized pins. However, surface demineralize pins can also be used with surface demineralized bores.

The body is then dried under clamp pressure and removed from the clamp. This pressure is provided by the clamps. The ambient air pressure may be above or below atmospheric pressure and is independent of the clamping pressure. The pins 90 (FIG. 1) are then inserted in the bores as described above.

During surgery, anterior end 18 of the implant 10, FIG. 1, is inserted first between the adjacent vertebra in the posterior approach. In this approach normally two incisions are made on opposite sides of the spine for corresponding separate implants. In the alternative, the posterior end may be inserted first in an anterior approach.

Figure 5:
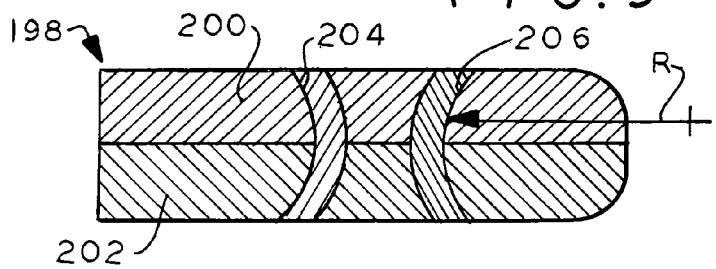
FIG. 5 is an sectional plan view similar to the view of FIG. 4 of an implant according to a second embodiment of the present invention.

In FIG. 5, an alternative implant 198 comprises planks 200 and 202 formed as described in connection with implant 10. The difference is that bores 204 and 206 are curved with radius rather than linear. The bores 204 and 206 each are mirror images of the other. The portion of bore 204 in plank 200 is also a mirror image of the portion in plank 202. The portion of bore 206 in plank 200 is a mirror image of the bore portion in plank 202. The curves of the two bores emanate from radii extending in opposite directions. The curvature of the bores is exaggerated for illustration and may be represented by straight bores inclined relative to each other in mirror image angles relative to the interface of the two planks 200 and 202.

A straight pin, such as right circular cylindrical pin 90, FIG. 17, is inserted into each the bores 204 and 206 which also are circular in cross section. The pins 90 when inserted into the bores 204 and 206 become bent. When bent they exhibit tension and compression as discussed above. The tensile and compressive beam loads form compression loads on the planks and frictionally hold the planks together. These loads are similar to the loads discussed in connection with pin 90, FIGS. 4 and 4a.

Figure 6:
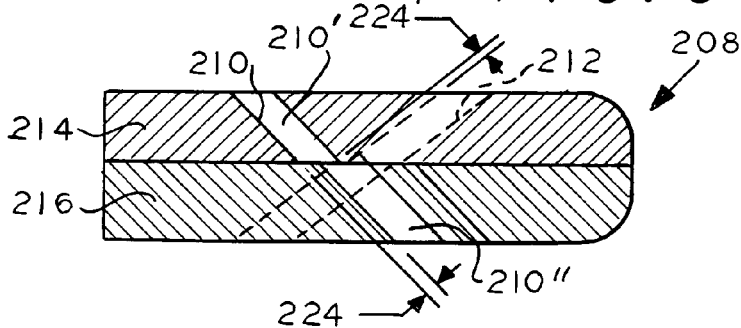
FIG. 6 is a sectional elevation view of the implant of FIG. 7 taken along lines 6-6.
Figure 7:
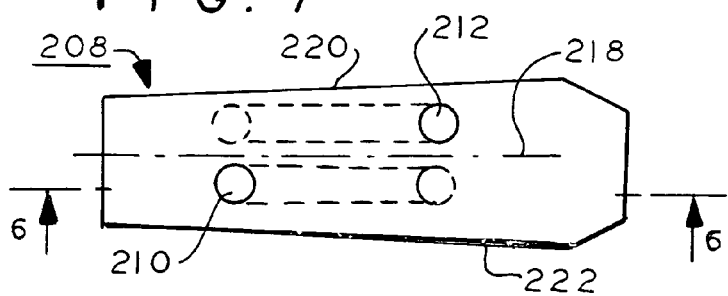
FIG. 7 is an side elevation view of an implant according to a third embodiment of the present invention.

FIGS. 6 and 7 illustrate a further embodiment of a locking bore arrangement. Implant 208 comprises two planks 210 and 212 of cortical bone as described for the implant of FIG. 1. The difference is the orientation and position of the bores for receiving the locking pins 90. The implant 208 has two bores 210 and 212. Bore 210 is oriented at about 45° relative to the plane of the interface between the planks 214 and 216 forming the implant. Bore 212 is oriented at the same angle but in the opposite direction as shown. Bore 212 is positioned medially between the longitudinal axis 218 of the implant 208 and side 220. Bore 210 is positioned medially between axis 218 and the side 222 opposite side 220. Both bores extend generally in the longitudinal direction of axis 218 as best seen in FIG. 7. The bores 210 and 212 in each plank have offset sections forming offset subsets of bores similarly as the bores of implant 10, FIG. 4. The bore section 210' of bore 210 in plank 214 is offset distance 224 from bore section 210" in plank 216. Similarly, the sections of the bore 212 in planks 214 and 216 are offset the same distance 224' as distance 224.

A straight pin similar to pin 90, but longer is inserted in each of the bores 210 and 212. These pins are each placed in tension and compression in response to their bending in a manner as described for pin 90 discussed above. The tension and compression loads of the pins transfer to the planks as axial compression load components in the direction of the implant longitudinal axis, frictionally holding the planks together. The bores 210 and 212 being in opposite orientation, restrain axial slippage of the planks in response to the pin compression loads which are exerted in opposing directions on the two planks. Thus the bending of the pin 90 as described in connection with FIG. 4a occurs also in the bores 214 and 216. The pins in the two bores 210 and 212 thus cooperate to hold the planks connected. In FIG. 6, note that the bore 210 forms a first elongated bore and the bore 212 forms a second elongated bore. The first and second elongated bores lie in spaced parallel planes as seen in FIG. 7. The projection of the first elongated bore 210 and the second elongated bore 212 in a direction normal to the planes (as depicted in FIG. 6) form an X shaped image of the two elongated bores in a plane parallel to the parallel planes (and to the drawing sheet).

Figures 8, 9, 10:
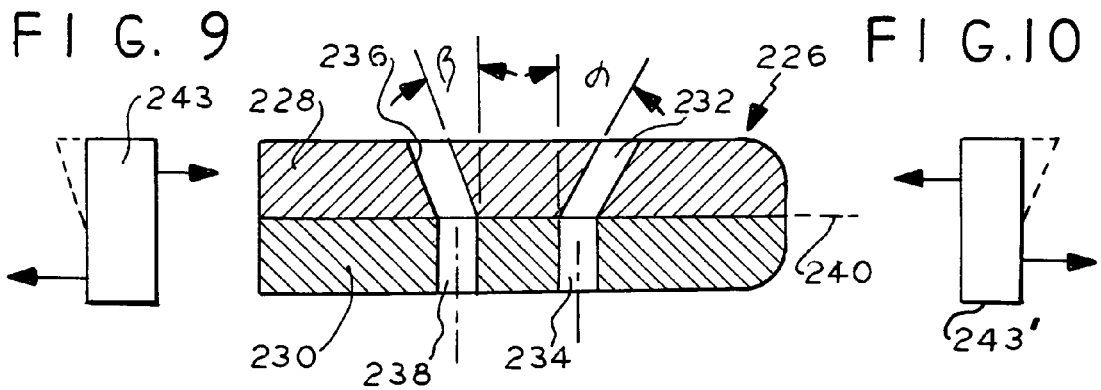
FIG. 8 is a plan sectional view of an implant according to a further embodiment of the present invention.
FIGS. 9 and 10 are side elevation views of an embodiment of locking pins used in the embodiment of FIG. 8.

In FIG. 8, implant 226 comprises two like mirror image planks 228 and 230 except for the bores therein. The planks 228 and 230 comprise cortical bone prepared as described above for the FIG. 1 embodiment. The difference is bores 232, 234, 236 and 238. Bores 232 and 234 form an offset subset identical to respective offset subset bores 236 and 238 and are oriented in mirror image relation along the longitudinal axis 240 of the implant. Bores 232, 234, 236 and 238 are all circular cylindrical and of the same diameter. Bores 234 and 238 are normal to the axis 240. Bore 232 is at angle α and bore 236 is at angle β to the axis 240 which angles are preferably the same value but oriented in opposite directions. In this case the offset is created by the different angles of the subset of bores forming a common bore.

A straight right circular cylindrical pin 243, FIGS. 9, 10 and 22, is inserted in offset subset bores 236 and 238 which are aligned at the interface of the planks 228 and 230. A second pin 243' identical to pin 243 is inserted in aligned offset subset bores 232 and 234. The pin 243 in response to the relative different angular orientations of the bores 236 and 238 is bent as shown in phantom in FIG. 9. Similarly pin 243' is bent as shown in phantom in FIG. 10. The bending of these pins creates tension and compression forces in each pin which create compression loads in the implant longitudinal axial directions of the arrows associated with the pins of FIGS. 9 and 10. These compression loads hold the planks 228 and 230 together due to the friction between the pins and the planks. The different angular orientation of the aligned bores in the planks 228 and 230 thus form an offset relationship of the bores similar to the offsets described in the embodiments above in the sense the offsets create equivalent compressive and tensile forces in the associated pins.

Figures 11, 13, 14, 15:
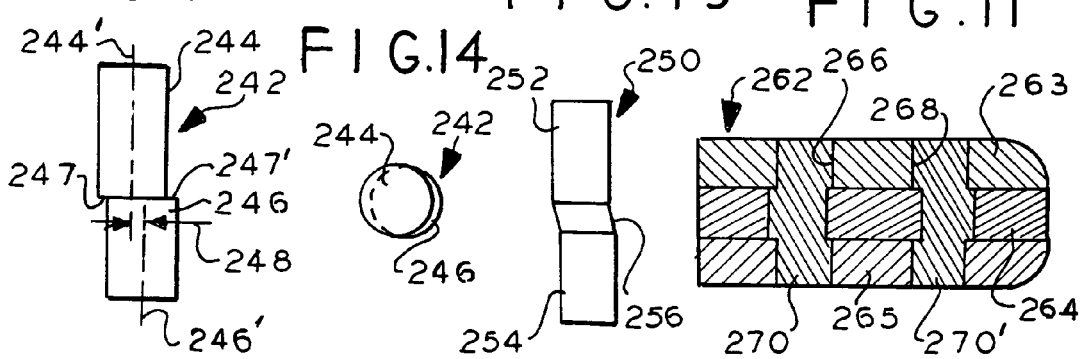
FIG. 11 is a plan sectional view of an implant according to a further embodiment of the present invention.
FIGS. 13 and 15 are side elevation views of locking pins according to further embodiments.
FIG. 14 is a top plan view of the pins of FIGS. 13 and 15.

In FIGS. 13, 14 and 30, in the alternative, pin 242 is used in multiple plank implants having a pin receiving bore (not shown) which is a straight through bore of a common diameter with no offset subset sections as in the above embodiments. Pin 242 has two sections 244 and 246. These sections are identical in diameter and are each right circular cylinders of cortical bone whose fibers run along the length direction as described for pin 90. Section 244 has a central longitudinal axis 244' and section 246 has a central longitudinal axis 246'. The axes are offset from each other a distance 248. The sections 244 and 246 are separated by a shoulder 247 which is planar and normal to the axes 244' and 246'.

When the pin 242 is inserted in a straight cylindrical bore, the sections 244 and 246 tend to bend in a direction normal to their axes creating compressive and tensile forces in the pin in similar fashion as the forces created in pin 90, FIG. 4a. These compressive and tensile forces create compressive forces in the mating planks which are held together as a result of the static friction loads between the pin and planks created by the plank compressive forces.

In a further alternative, pin 250, FIG. 15, has two offset right circular cylindrical sections 252 and 254. These sections are also offset a distance such as the distance 248 of pin 242, FIG. 13. Pin 250 sections 252 and 254 are not separated by a planar shoulder such as shoulder 247 between the sections 244 and 246 of pin 242. Instead, the sections 252 and 254 are interconnected by inclined section 256. Section 256 is circular in transverse section. Section 256 has an axial extent sufficient to provide a taper between the sections 252 and 254 which provides a gradual interface between the sections and which permits the pin 250 to be easily inserted in a straight bore of one diameter.

Figure 12:
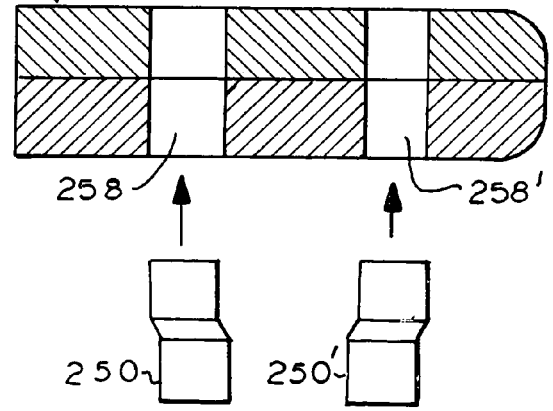
FIG. 12 is a plan sectional exploded view of an implant of a further embodiment of the present invention.
Figure 16:
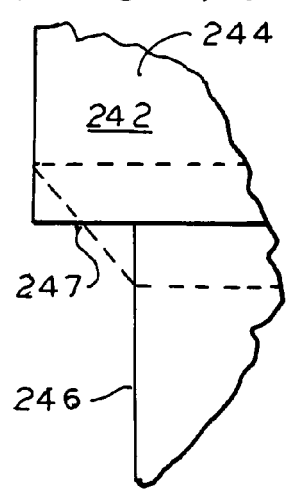
FIG. 16 is a more detailed view of a portion of the pins of FIGS. 13 and 15.

For example, in FIG. 12, two identical pins 250, 250' are inserted in corresponding identical bores 258, 258' in implant 260 which is otherwise identical to implant 10, FIG. 1. FIG. 16 shows the interface region between the two sections 244 and 246 of pin 242, FIG. 13 in more detail. The dashed line shows the interface region of the sections 256, 258 and 254 of the embodiment of FIG. 15. The pins of both embodiments of FIGS. 13 and 15, when inserted in the bores 258 and 258' of FIG. 12, bend and create the compression and tensile loads in the pins which lock the pins to the planks of the implant 260.

In FIG. 11, implant 262 comprises three cortical bone planks 263, 264 and 265 prepared similarly as the planks of implant 10 except for the bores. The implant includes a third central plank 264 whose posterior end is flat whereas the posterior end of the planks 263 and 265 are curved with radii as shown in the figure. The implant has two bores 266 and 268. The bore 266 is identical to the bore 268 except it is in mirror image relation in the implant and are longitudinally axially spaced from each other. Each bore 266 and 268 is in three sections. Each section is in a corresponding plank 263, 264 or 265. The bore sections are each identical in diameter but are offset as shown. The bore sections in exterior plank 263 are axially aligned with the bore sections in exterior plank 265 in a direction normal to the longitudinal implant axis. The bore sections in interior plank 264 are offset axially in the longitudinal direction of the implant from the bore sections in the exterior planks. The amount of offset is as described above for the implant of FIG. 4. The offsets of the bore sections in interior plank 264 are displaced in opposite directions relative to each other in the longitudinal implant direction.

Right circular cylindrical pins 270 and 270' of cortical bone are fabricated to about the same dimensions, preferably as close in dimensions as possible, it being recognized that it is difficult to fabricate bone elements as identically as metal components. The pins 270 and 270' are inserted into corresponding bores 266 and 268 which preferably are the same, but in practice may differ in dimensions due to the fact the bores are formed in bone. These pins are bent by the offset relation of the bore sections creating compressive and tensile loads in the pins which transfers into compressive loads on each of the planks. These loads hold the planks together.

In FIG. 21, cortical bone pin 270 is similar to pin 242, FIG. 30 except it has a cap 272 at one end. The pin 270 has two offset pin sections 274 and 276 which are offset similarly as pin 242. The cap 272 is disc shaped and may be recessed in a countersunk bore (not shown) in the mating implant. The cap assists in preventing the pin from migrating through the mating implant bore in at least one direction.

In FIG. 23, pin 278 is cortical bone which is formed in a curved bent configuration with a radius 280. This pin is preferably used with a straight right circular cylindrical bore in the mating implant planks such as with implant 260, FIG. 12, or may be used with offset bore sections in a bore such as the bores in the implant of FIG. 4. The curved pin would be inserted in the offset bore with the curvature extending in a counter direction of the offset direction of the bores to provide increased compressive loads. Not shown are edge chamfers on the various pins which may be provided to facilitate insertion into the various bores.

FIG. 24 shows a three edged pin 282 whose edges 283 extend in the pin axial direction as radially extending ribs. The pin 282 has parallel flat end surfaces and a curved peripheral surface between the edges 283 which surface may be a circular segment or a segment of some other curve such as an ellipse and so on. This pin is inserted in a right circular cylindrical bore in the implant. The edges 283 lie on a diameter greater than that of the mating bore so as to dig into the surface of the bore to provide interference frictional fit with the bore. The external surface of this pin need not be demineralized or at least the edges masked from such demineralization.

FIGS. 25, 26 and 27 show respective square, hexagonal, and elliptical (284) in transverse cross section pins having straight longitudinal axes. These pins are inserted in right circular cylindrical bores having a diameter less than the largest transverse dimension of the pin so that the pin is in compressive interference with the body of the implant in the bore. The corners of the square and hexagonal pins dig into the mating bore surface of the implant. The elliptical pin 284 is shown in dashed lines in FIG. 32 and the bore is shown in solid line. The bore is circular cylindrical. The edges of the small radii end of the pin are in compressive interference fit with the bore surface of the implant.

Figure 26A:
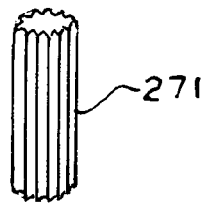
Figure 26B:
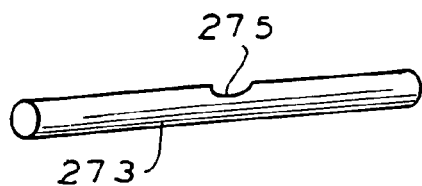
Figure 26C:
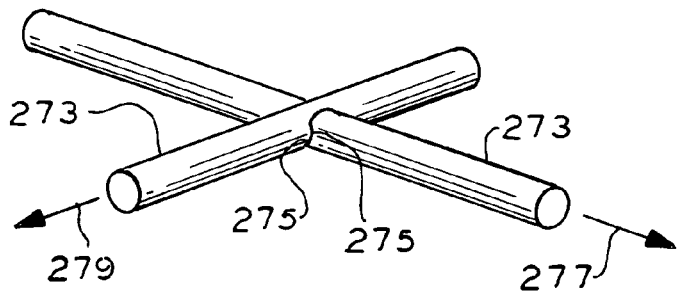
FIGS. 26c and 26d are respective isometric views of two of the pins of FIG. 26b interlocked and as employed with a multiple layered implant for securing the layers of the implant together.
Figure 26F:
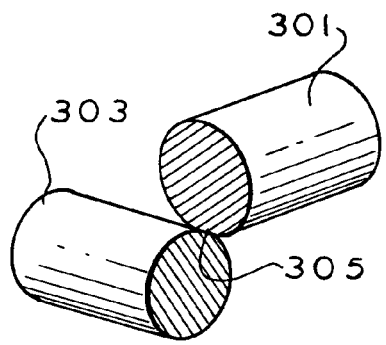
FIGS. 26e-26f are an isometric view of crossed pins and a more detailed cross section view of the crossed pins, respectively.

Pin 271 of FIG. 26a is fluted with the flutes running approximately parallel to the longitudinal axis of the pin. Pin 273 of FIG. 266 has a transverse groove or channel 275. Channel 275 is a segment of a circle or approximates such a segment. In FIG. 26c, two pins 273 intersect at a right angle with their channels 275 interengaged, by way of example, and may intersect non-perpendicular to each other at other angles. These interengaged pins thus are locked to preclude axial displacement in directions 277 and 279 relative to each other. The pins 273 can be used to attach the layers 267 of implant 269, FIG. 26d, together. The pins 273 each optionally may be press fit into the mating bores of the implant 269 to provide a friction interference fit. The pins are pliable bone so that they may ride over one another as they are inserted in the mating bores until the channels 275 overlie each other and interlock. This interlock locks the pins to the implant. Once locked, the layers 267 can not easily separate and the assembly forms a reliable unit.

Figure 26D:
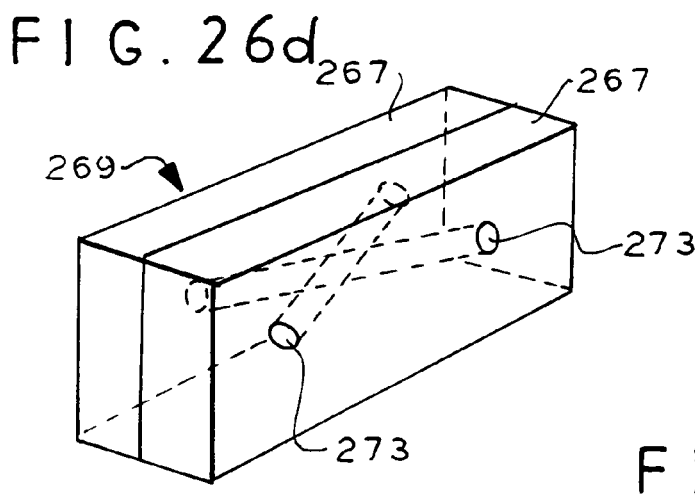
Figure 26E:
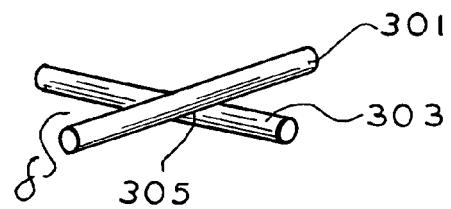

In FIG. 26e, pins 301 and 303 are assembled to an implant (not shown in this figure) similar to the implant 269 of FIG. 26d. The implant comprises multiple layers which are held together by the pins 301 and 303. These pins preferably have smooth surfaces such as pin 90, FIG. 17, but may have roughened surfaces as pins 304 and 308, FIGS. 19 and 20, respectively. The two pins are assembled in crossed angular relation, angle δ which may be about 60°, for example. The pins cross each other in interference fit so that the contact region 305 may be compressed somewhat by the compression loads imposed by the pins on each other. The bores in the implant for these pins thus intersect to provide this interference during assembly.

Pin 285 of FIG. 28 is similar to the pin 282 of FIG. 24 except the edges 283 of pin 282 are rounded in pin 285.

In FIG. 29, pin 286 is similar to the square pin of FIG. 25 except the corners are rounded. The rounded corners 286' dig into the surface of the mating bore of the implant to provide interference compressive fit which frictionally locks the implant planks together.

In FIG. 31, pin 288 comprises two sections 290 and 292 which are mirror images of each other. Section 290 has a longitudinal axis 293 and section 292 has a longitudinal axis 294. The axes are inclined relative to each other at an angle δ. This pin has sections similar to the bores of the implant 226 of FIG. 8. However, each section 290 and 292 is inclined relative to a plane 295 at the interface of the two sections. The angle δ preferably may have a value in the range of 1-10° as do the corresponding angles of the various bores and pins described in the above embodiments in which a section of the bore or pin is inclined relative to a plane parallel to the implant plank interface. This angle of inclination range is also applicable to the curved pins or bores such as pin 278, FIG. 23 or bore 204, 206, FIG. 5 including the angles α and β, FIG. 8. The value of the angle is a function of the pin material and its brittleness and its ability to compress so as to distort and bend as applicable without fracturing the associate pin. The same rationale is also applicable to the values of the offsets of the pins and bores. The pins must be able to distort and bend without fracturing under tensile and compressive loads.

Pin 296, FIG. 33, is circular cylindrical with a plurality of radially extending ribs 298. The ribs 298 extend for the length of the pin in this embodiment but may be foreshortened in other embodiments by removing the shaded material. the shaded regions on a given rib would be repeated on all of the ribs which would be identical. In the alternative, ribs comprising the shaded regions may be mixed on a given pin as desired. The ribs have rounded edges with sides that slope inclined toward the main pin circular body or are normal to the body at the junction therewith.

In use, the pin 296 is inserted in an implant bore that is straight and of a diameter that is the same as the diameter of the body of the pin from which the ribs 298 project. In this way, the ribs are either compressed by the implant in the implant bore or dig somewhat into the bone of the implant in the bore to provide compressive locking of the pin to the implant planks locking the planks together.

In FIGS. 18-20, respective pins 300, 304 and 308 have corresponding respective external threads 302, an external knurled surface 306 or a roughened external surface 310 to further assisting the pins to grip the mating bore surfaces in an implant. The surface 310 may comprise a plurality of small projections and/or dimples such as may be provided by compressing or otherwise texturing the surface with a textured material having a granular surface somewhat like sandpaper. Such surfaces may be provided to pins of the different shapes as described above where practical. The pin peripheral surfaces may be entirely or partially roughened.

Figure 40:
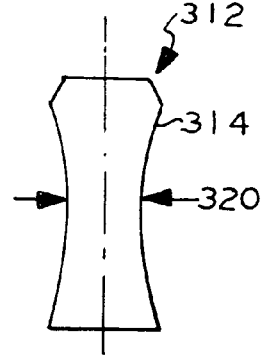
Figure 41:
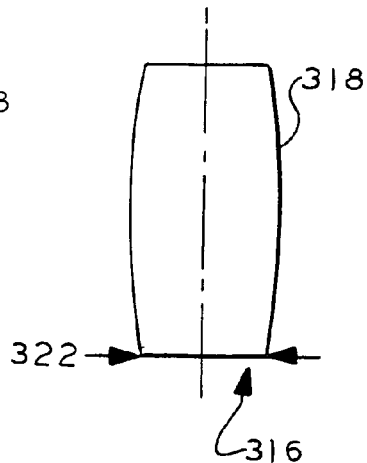

In FIG. 40, pin 312 has a concave annular surface 314 and in FIG. 41 pin 316 has a convex annular surface that resembles a barrel shape. In use, these pins are inserted in an implant bore that is circular cylindrical of a diameter that is the same as about the smallest diameter of the pins. In pin 312, the implant bore has a diameter of about the size of dimension 320 and in pin 316 the mating bore has a diameter of about the size of dimension 322.

Pins with different cross sectional geometries can be used to relieve stresses as the bone planks shrink upon drying, which tends to minimize the development of cracks in the planks. Such pins with different cross sectional areas than the mating bore in the implant are as shown in FIG. 71 and can be used to obtain a friction fit. In FIG. 71 pin 410, of square cross section (FIG. 25) is placed in a circular bore 412 of implant 413. Other pins with different shapes were discussed in connection with FIGS. 25-29, for example, to obtain friction fits with the mating bores. The spaces around the pins provide the desired stress relief as the bone planks shrink to minimize the cracking of the planks.

While pins have been described made of cortical bone, the pins may be made of other biocompatible materials such as polymers, metals and other known biocompatible materials. Further, the ends of the pins can be spread apart to also increase holding power. Punching the end of a pin is one way to achieve such spreading. Such swaging relationships for example are utilized in the metal fabrication art. In addition, wedges, or smaller pins (not shown) may be employed to spread the ends of the inserted pins apart. These further pins and wedges are made of the same or biocompatible material as the pins.

In the above embodiments, the pins and offset bores, where the term offset includes both offset axes and angular differences in sections of a bore receiving a pin, have closely matching diameters so that there is negligible interference fit between any of the pins and the corresponding bore diameter. Thus the holding power is provided with little or no diametrical interference between the pin and the mating bore. The tensile and compressive bending loads in the bent pin, due to either pin bent shapes as shown in FIG. 23 or 31 or offsets of pin section axes, creates compression loads in the mating implant bone fibers without inducing undesired splitting.

Figure 63:
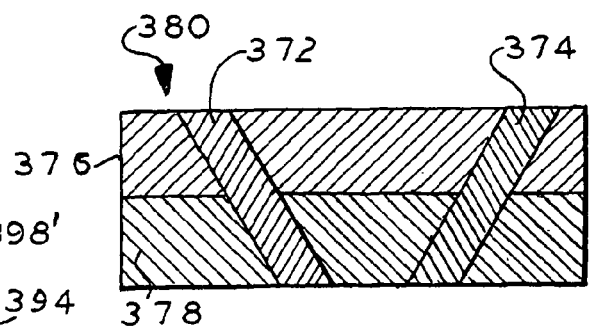
Figure 64:
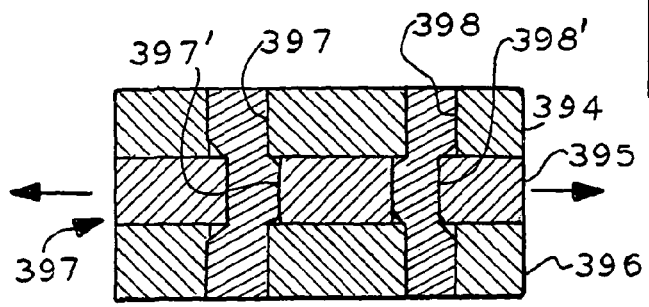
Figure 65:
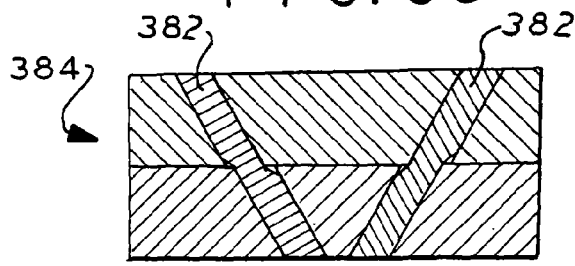

Holding power is increased by establishing an angle between the pins as shown in FIGS. 6 and 7. Angled pins have the property that they oppose separation of the planks by virtue of their geometry. This reduces the burden of friction fitting the pins to just being able to keep the pins from shifting or falling out of the respective bores. This arrangement is considerably easier to implement than holding the plates together, FIGS. 6-8, 63 and 65-67. In FIG. 63 two pins 372 and 374 are placed in corresponding bores in planks 376 and 378 of implant 380. Even without interference fit, this arrangement has increased holding power for the plates. The holding power is thus significantly increased in the embodiment of FIG. 65 wherein the straight cylindrical pins 382 are in opposing offset angled bores of implant 384. In FIG. 67, implant 386 has two offset bores 388, 389 wherein bore 388 is generally normal to the interface 392 between planks 390, 391 and bore 389 is at an acute angle to the interface, i.e., non-perpendicular. In FIG. 64, the three planks 394, 395 and 396 of implant 397 are similar to the arrangement of the FIG. 11 implant except the bores 397, 398 thereof are arranged with the offset sections 397' and 398' 180° in opposite directions from that of the FIG. 11 implant embodiment.

In FIGS. 68-70, a tool is shown for forming bone pins. Pins may be also be formed with a core saw, i.e., a circular cylindrical saw blade. However, there may be some dimensional variations among saws and this can lead to an unacceptable variation in pin diameters among the different pins made on different saw blades. In the figures, the tool 400 resolves this dimensional variation problem.

Tool 400 is a tool steel die used to finish bone pins to a final diameter. In FIG. 69, the die 400 has a bore 402 which terminates at smaller diameter bore 404. Bore 404 terminates at conical bore 406 in recess 408. In use, all pins are fabricated slightly oversize in diameter. These pins are then forced through the bores 402, 404 and 406. The smaller diameter bore 404 shaves the pins to a standard diameter of this bore. The larger diameter bore 402 protects the pin from spreading by enclosing it while the pin has an axial force applied thereto.

Figure 70A:
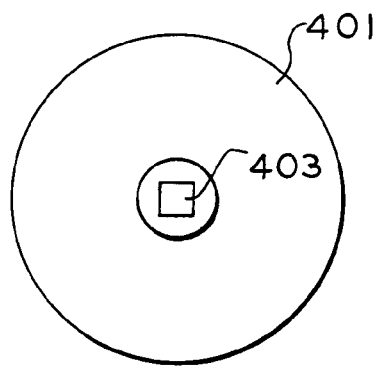
FIGS. 70a-70d are plan views of further embodiments of the tool of FIGS. 68-70.
Figure 70B:
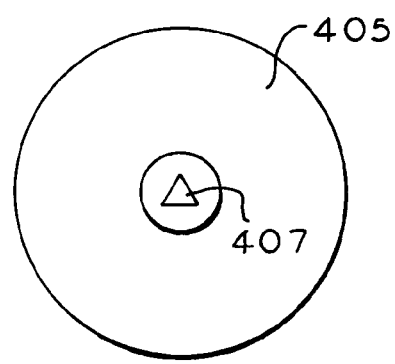
Figure 70C:
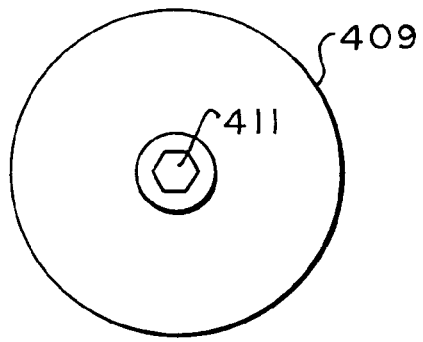
Figure 70D:
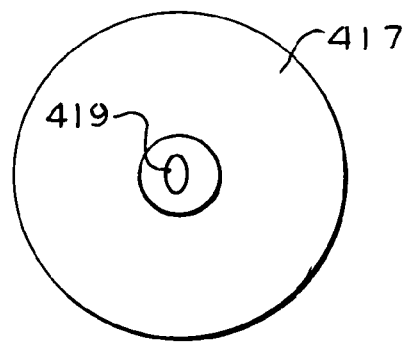

In FIG. 70a, a tool die 401 is similar to tool 400 except that the pin forming die bore 403 is square to form a square pin such as pin 410, FIG. 25. In FIG. 70b, die 405 has a triangular bore 407 for forming a triangular in section bone pin. In FIG. 70c, die 409 has a sextuplet bore 411 for forming pin 415, FIG. 26. In FIG. 70d, die 417 has an oval bore 419 for forming pin 284, FIG. 27. Should the pins prior to forming have a relatively large transverse cross section, then the pin may be shaped by a series of dies (not shown) having progressively smaller bores for shaving the pins to the desired shape and size gradually. This progressive forming minimizes damage to the bone that might otherwise occur. Such progressive forming may also be applied to the corresponding bores wherein the bores may be formed relatively small in diameter and the diameter progressively increased until the desired diameter is obtained.

Bores may be formed by broaches (not shown) which differ slightly in diameters or shaped cross sections. The final bore shape and dimensions are thus obtained by gradual incremental formation. Alignment devices may be used to align the pin being formed with the die bores. Such dies may comprise a series of stepped dies axially aligned to progressively form the pins or bores. The shapes of the bores and pins may also be gradually changed progressively, for example, from a rectangular cross section to circular, triangular or polygon for example, in small incremental steps. The dies are accurately formed to form the bores and pins to precise dimensions required for a given implementation.

For deep bore cuts, a tapered broach or a series of broaches, each slightly larger than the immediately preceding die can be used. In forming bores, first a hole is drilled of a diameter about the smallest dimension of the desired bore geometry. Then a shaped broach forms the final bore configuration.

Figure 34:
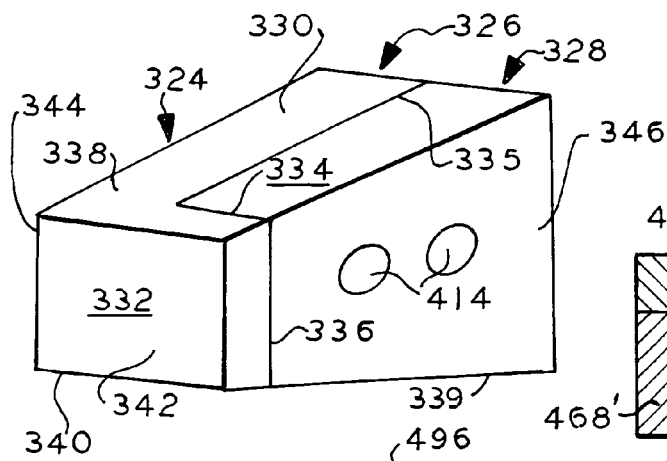
FIGS. 34 and 36 are isometric views of implants according to further embodiments of the present invention.

In FIG. 34, implant 324 preferably comprises two cortical bone members 326 and 328. Member 328 is formed from a flat plank as described above in connection with FIGS. 60 and 61, such as plank 44 or formed as described in connection with FIGS. 87-89. Member 326 is more complex and is L-shaped. Member 326 has a base portion 330 and a leg 332 which extends at a right angle to the base portion. Leg 332 has an inner surface 334 facing the surface 335 of the base portion 330 forming a recess 336. The member 328 fits into the recess 336. The surfaces 338 and 340 taper toward each other and toward the posterior end 342 to form a wedge shape. The sides 344 and 346 are parallel. the surfaces 338 and 340 may also be grooved (not shown).

Figure 55:
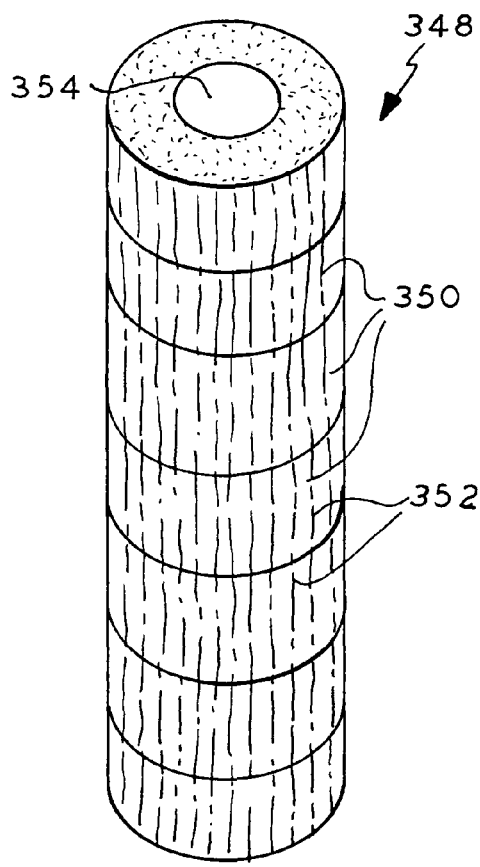
FIG. 55 is an isometric diagrammatic view of a long bone illustrating the fabrication of implants according to various embodiments herein.
Figure 56:
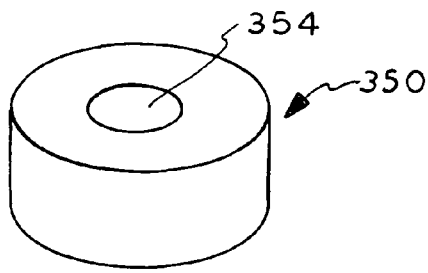
FIGS. 56-58 illustrate in isometric views various sequential steps in fabricating the implant of FIG. 59.
Figure 57:
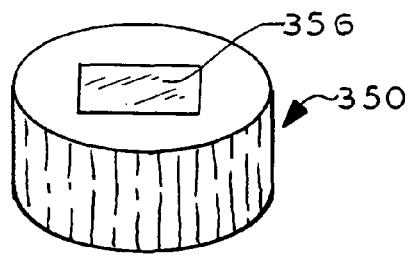
Figure 58:
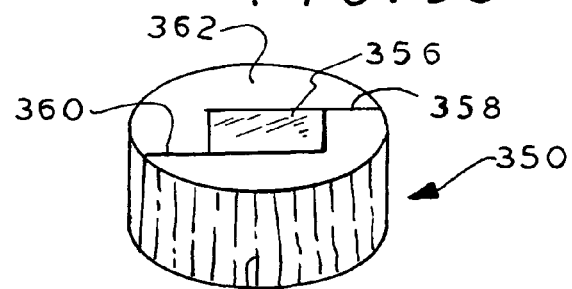

The L-shaped member 326 is formed as shown in FIGS. 55-59. In FIG. 55, a long bone 348 of a donor is schematically represented. The bone 348 is sliced into a plurality of rings 350. The fibers 352 extend in the longitudinal direction of the long axis of the bone. The ring 350 appears as shown in FIG. 56 wherein the central opening 354 is formed by the femoral or medullary canal. In a first step, FIG. 57, the canal 354 is reshaped as a rectangular opening 356. The opening 356 is formed by a broaching tool as well known in the machine tool fabrication art. In FIG. 58, two saw cuts 358 and 360 are made to form the broached ring into two L-shaped bodies 362 and 364. The two L-shaped bodies are then finished into the an L-shaped member 366, FIG. 59, having a base 368 and a leg 370 extending from the base.

The member 328 may be formed from a band saw from cortical rings or cortical strips and sanded to fit into the desired shape and dimensions to fit in the recess 336, FIG. 34.

Figure 37:
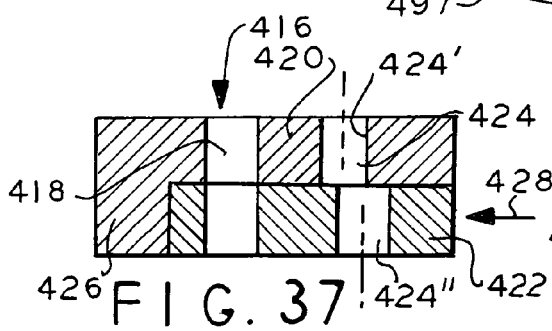
FIGS. 37 and 38 are respective top plan views of the implants of FIGS. 34 and 36.
Figure 38:
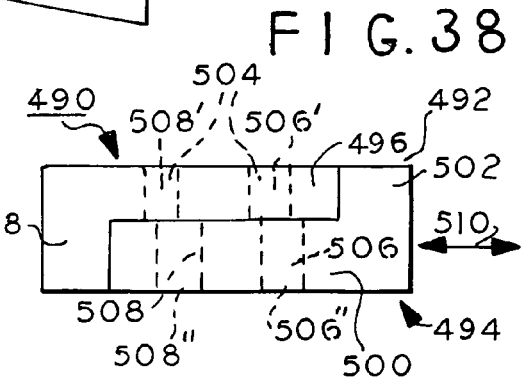

In the implant 324, two pins 414 are inserted into corresponding bores through the base portion 330 and the filler plank member 328. Both bores may be offset as shown in FIG. 2. In the alternative, in FIG. 37, implant 416 has one optional through bore 418 through the base portion 420 and flat plank filler member 422 and is of constant diameter. A second bore 424 is offset as bore 52, FIG. 4. The offset of bore 424 is such that the axis of bore 424' is closer to leg 426 than bore 424" in member 422. This offset relationship forces the straight pin inserted in bore 424 to force the member 422 in direction 428 against the leg 426. The optional straight pin-bore combination of bore 418 may be eliminated if desired or if used may be used with the various different shaped pins of FIGS. 21-33 to provide enhanced gripping of the mating bone planks.

In FIG. 72, an implant 430 has an L-shaped member 432 and a flat plank filler member 434. This implant has two offset bores 436 and 438. Bore 436 has offset bores 436' and 436".

Bore 438 has offset bores 438' and 438". In FIG. 72, by way of example, the dimensions may be as follows:

1) C<D

2) $(A-B) > \frac{D-C}{2}$

Where in general D−C=about 0.2 mm for 3 mm diameter pins.

The net result is that the forces on the two pins oppose each other and lock the pins to the planks.

Figure 62:
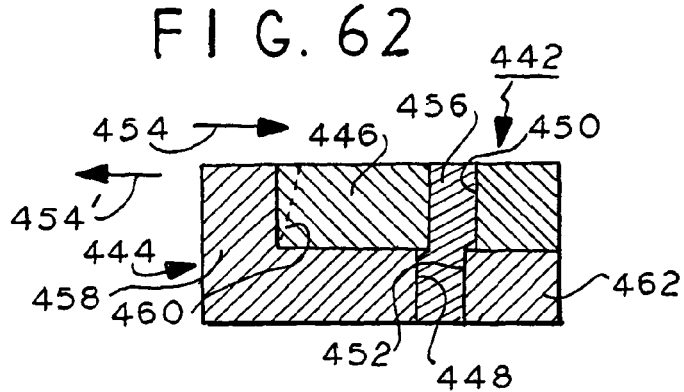
FIGS. 62-65 and 67 are sectional plan views of different embodiments of implants according to the present invention.

In the alternative, in FIG. 62, implant 442 employs an L-shaped bone member 444 and a flat filler plank member 446. The implant may have the overall shape of implant 324 of FIG. 34. The difference is that implant 442 has a single offset bore 448 similar to bores 52 and 54, FIG. 4 discussed above. The offset of subset bore 450 to subset bore 452 is in direction 454. The offset of bore 450 bends the normally straight pin in direction 454. As a result, the bend in the pin creates a compression load in the member 446 in direction 454'. This compression load forces the member 446 against the leg 458 of the member 444, locking the plank member frictionally against the leg 458, which may be roughened slightly to increase the friction load thereon imposed by member 446. Also, the leg 458 may have an inclined surface as shown in dashed line 460 to wedge the plank member 446 against the surface of base portion 462 of member 444. The member 446 may also have a complementary inclination at the end surface abutting the leg 458.

The net result is that the plank 446 is forced against the leg 458 of member 444. Bore 436, FIG. 72, may thus be omitted to further increase the force against the leg 458 induced by pin 414 in bore 438 since a pin in bore 436 tends to displace the plank 434 away from the leg 440. Preferably, two bores are offset in the same direction as bore 438 wherein a bent pin in both bores reinforce each other in displacement of the plank 434 against the leg 440 holding the planks in tighter relationship.

This implant is strong during insertion and while supporting spinal loads. Employing a single L-shaped member with a flat plank filler member provides advantages in ease of assembly and yet provides a relatively strong implant during insertion. Assuming the wider end is the anterior end which is inserted into the disc space first, the insertion forces on the member 328 does not displace this member relative to member 326 since it abuts the member 326 leg. The two pins 414 resist axial displacement of the member 326 relative to member 328 during insertion due to insertion loads. Since only one member 326 might displace relative to the other member 328 except for the pins, the leg helps resist insertion shear loads on the pins to preclude failure during insertion. However, the selection of bone for the filler plank and the L-shaped member may be more critical in that the bones should be matched so that they react uniformly in response to changes in the environment. Bone separation due to such changes is not desirable.

Figure 35:
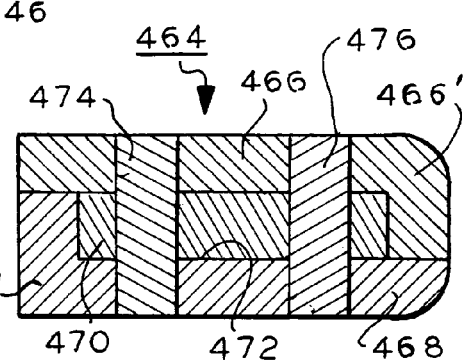
FIG. 35 is a plan sectional view of an implant according to a further embodiment.

In FIG. 35, in a further embodiment, implant 464 comprises two outer L-shaped members 466 and 468 and an inner third layer plank member 470 which is planar. The member 470 fits closely in the recess space 472 between the two outer members 466 and 468 formed by their respective legs 466' and 468'.

Two pins 474 and 476 are placed in respective aligned bores in the members 466, 468 and 470. The pins 474 and 476 are normally right circular cylinders of cortical bone. The corresponding bores are offset as shown in FIG. 64 by way of example. In further alternatives, the bores may be offset and/or at angles as in FIGS. 63, 65 and 67. In a further alternative, the pins may be bent as in FIGS. 23 and 31 or of other shapes as shown in FIGS. 21 and 24-33. Further, the offset may be in opposite directions to the offset illustrated in FIG. 64 so that the pins are bent in opposite directions to the pins of the embodiment of FIG. 64. The result is still opposing forces created by the two pins. This embodiment has the same advantage during insertion as the embodiment of FIG. 34. Here, the leg 466' abuts the central member 470 which abuts the leg 468'. Thus insertion loads are resisted by member 468 that are exerted on the central member 470 and on member 466. Only member 468 might displace in response to insertion forces thereon to the left in the figure. Such forces are resisted by the two pins 474 and 476. Thus only part of the insertion load is borne by the pins.

Figure 39:
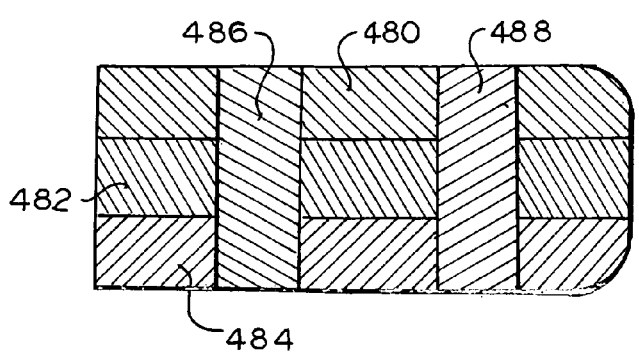
FIG. 39 is a plan sectional view of an implant according to a further embodiment.

FIG. 39 illustrates a three layer implant 478 comprising three flat planks 480, 482 and 484. This implant is by way of example as more than three planks may also be used. The planks are joined by two pins 486 and 488. The pins 486 and 488 are shown as circular cylindrical inserted into offset bores. The offset is as described in connection with FIGS. 35 and 64, for example. In all of the above implants, the exterior surfaces are formed into wedge shapes with two opposing tapered sides as in the FIG. 1 embodiment or with straight sides on all sides. Further, the implants as described above and below herein may have further surface features for receiving implant insertion tools as known in this art. Such features may included threaded bores and/or slots or channels for receiving mating insertion tool complementary features for temporarily securing the implant to the insertion tool. The planks of this implant can each displace longitudinally in response to insertion loads in case of pin failure. The two pins absorb all of the relative differences in insertion forces on the three planks.

Figure 36:
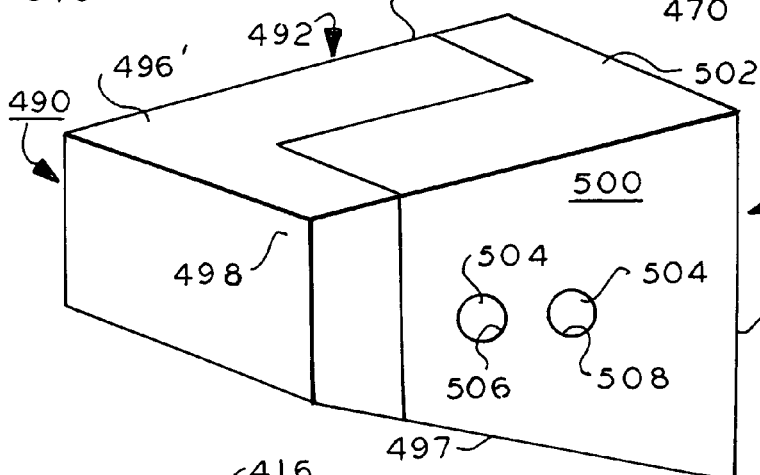

In FIG. 36, a further embodiment of an implant 490 comprises two mating L-shaped cortical bone members 492 and 494. Member 492 includes a base member 496 and a leg 498. Member 494 includes a base member 500 and a leg 502. Two cortical bone pins 504 are inserted into two mating offset bores 506 and 508. Bore 506 comprises bore 506' in member 496 offset from bore 506" in member 500. Bore 508 comprises bore 508' in member 496 and bore 508" in member 500. Bores 506' and 508' are each offset in the same direction of directions 510 relative to bores 506" and 508" respectively. This same direction of the forces reinforce each other to double the holding power of a single pin.

The legs 498 and 502 abut the base portions of the respective members 496 and 500 to preclude axial displacement of the members toward each other in directions 510. The pins 504 bend in a direction so that the leg 498 is forced against the member 500 and the member 496 is forced against the leg 502 in one of directions 510 to the right in the figure. During assembly, the base portions of the various embodiments employing an L-shaped member are pressed against each other without applying a force to the legs to provide even pressure between the base members during assembly.

In this embodiment, the anterior end 495 is inserted first into the disc space and the member 500 absorbs all of the insertion loads. There is no or negligible insertion load on the member 492. Therefore, there is little shear force on the pins at the junction between the members 496 and 500 as compared to the embodiment of FIG. 34.

In the embodiments of FIGS. 34 and 36, the upper and lower surfaces of the respective implants facing respectively toward the top and bottom of the drawing figure are tapered forming a wedge shape. The upper and lower surfaces may be grooved as in the embodiment of FIG. 1. These upper and lower surfaces abut the vertebra. The pins are horizontal relative to the vertebra and generally parallel thereto. In this case the insertion load is applied against the upper and lower surfaces 338 and 339, FIG. 34 or surfaces 496' and 497 in the implant 490 of FIG. 36. The edges of the members 494 and 496, FIG. 34, or the edges of the members 494 and 496, FIG. 36, of implant 490 engage the vertebra. It is preferable that the bone fibers run vertically between the surfaces 496' and 497 and normal to the longitudinal axes of the pins 504 to preclude shearing action as shown in FIGS. 79 and 81 during insertion. The fiber direction then would run as shown in FIG. 82 relative to the pins. The fact that the pins and bores are substantially the same diameter precludes the splitting shown in FIG. 82.

Figure 42:
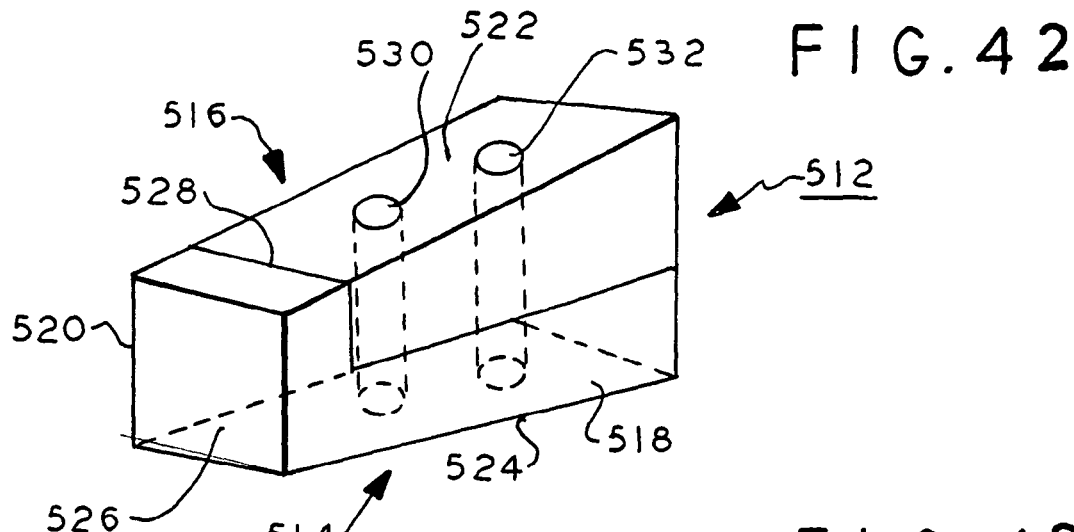
FIGS. 42-49, 52 and 53 are respective isometric views of implants according to further embodiments.

In FIG. 42, in the alternative, implant 512 includes an L-shaped member 514 and a plank member 516. The L-shaped member 514 has a base member 518 and a leg 520 at one end of the base member. The implant has tapered surfaces 522 and 524 which converge at posterior end 526. Surface 522 includes a surface of the leg 520 and a surface of the plank member 516. These tapered surfaces as in all of the embodiments are formed after the plank members are assembled. In this embodiment, the plank member 516 fits in the recess 528 formed by base member 518 and the leg 520. Therefore, the broad surfaces 522 and 524 abut the adjacent vertebra instead of the edges as in the embodiments of FIGS. 34 and 36.

The implant 512 has two pins 530 and 532 which are in the vertical orientation relative to the vertebra when the implant is inserted. The pins are offset and the mating bores are straight cylindrical bores as in the embodiment of FIG. 12 or the pins are straight circular cylinders and the bores are offset as in FIG. 4. In a further embodiment one pin may be offset and one pin may be at an angle or both pins at an angle as disclosed in the various embodiments discussed above.

Figure 43:
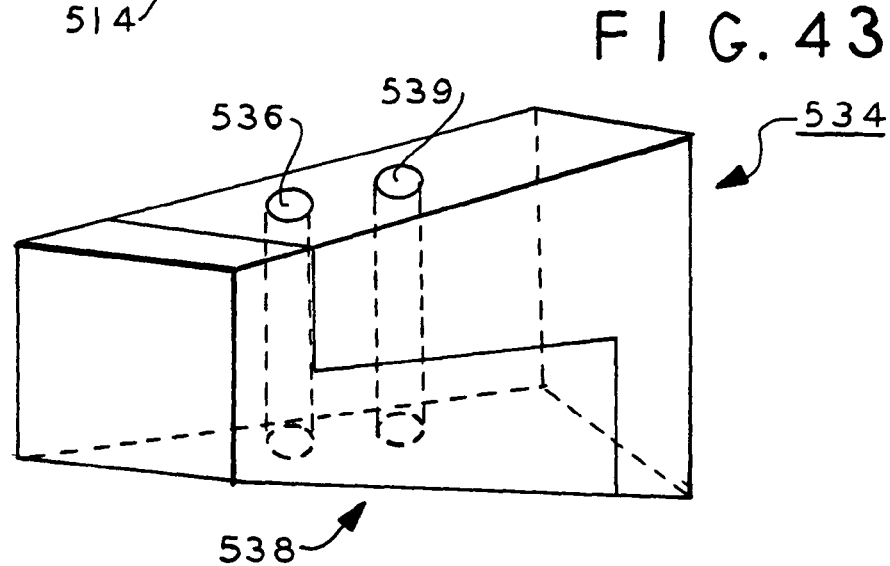

Implant 534 of FIG. 43 is similar to implant 490, FIG. 36. Implant 534 differs from the implant 490 by way of orientation with respect to the insertion direction of the implant. As in the embodiment of FIG. 42, the two pins 536 and 538 are oriented vertically with respect to the insertion direction so that the pins abut the adjacent vertebra. The implant 534 and pins are cortical bone. Either the pins are offset as in FIG. 12 or the bores are offset as in FIG. 4. In other embodiments, there may be a single pin or the pins may be at different angles as in FIGS. 63 and 67. Also, all other embodiments of pin shapes, offsets, angles and direction of offsets as discussed above are applicable to this embodiment.

Figure 44:
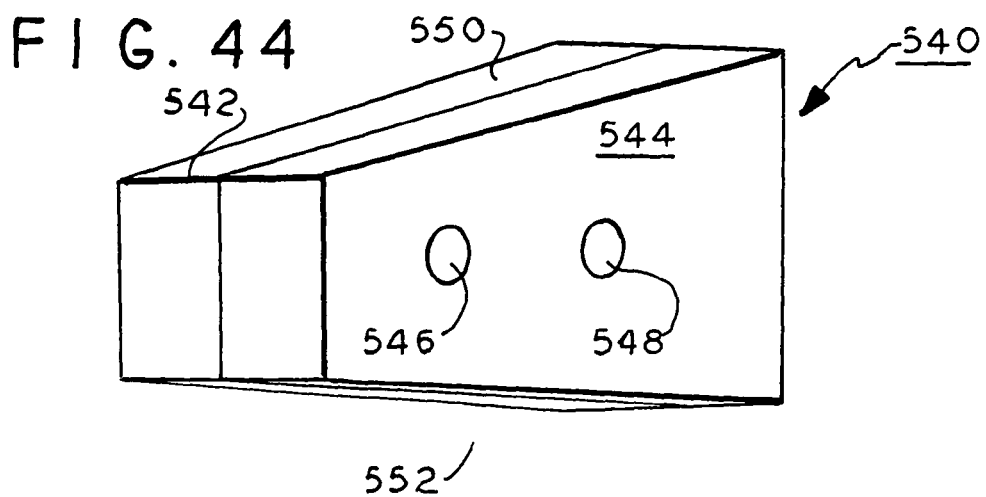

FIG. 44 illustrates implant 540 which comprises two planks 542 and 544 attached by pins 546, 548. The planks are in the form of a wedge with tapered opposing surfaces 550 and 552. This implant differs from the implant of FIG. 1 in that the gripping teeth 20 of FIG. 1 are omitted. The pins of this embodiment are offset the same as the pins of the implant of FIG. 1. The sides of the implant may also be tapered. Further, the insertion end may be chamfered to facilitate insertion. One or more of the planks can be fully or partially demineralized before assembly in this embodiment and that of FIG. 1. A fully demineralized plank may in some cases be encased by partially demineralized planks which partial demineralization should be a minimum if so used. For example, the central plank in FIGS. 35 and 39 may be fully demineralized. This implant is strong for supporting spinal compression loads and is reasonably stable under rotational loads with the advantage going to the implant with the fewest layers, two as compared to three, for example. This implant is easy to fabricate. However, this embodiment may be wasteful of bone. Also, it may be weak in insertion load resistance wherein the pins might absorb most of the insertion forces.

Figure 45:
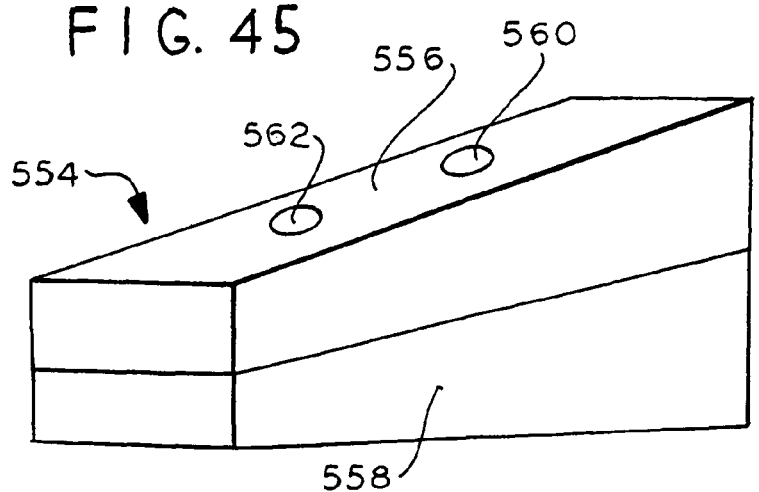

In FIG. 45, implant 554 comprises two planks 556 and 558 of cortical bone and two cortical bone pins 560 and 562. Here, the planks are oriented so that their broad surfaces engage the adjacent vertebra instead of the edges as in implant 540 of FIG. 44. The pins are vertical with respect to the vertebra orientation after insertion into the disc space. The pins are offset as described above in the various embodiments.

In this embodiment, the planes of the planks are parallel to the vertebra and is strong in supporting compression loads exerted by the vertebra. It is expected that this implant is rotationally stable which increases with two members instead of three. It is easy to fabricate and with respect to the embodiment of FIG. 44, there is less chance of layer separation because the layers are mainly under compression rather than shear. Bone planks formed from a long bone parallel to the bone axis from which they are cut are believed to be advantageous for this embodiment as compared to the vertical oriented planks of FIG. 44. However, like the FIG. 44 embodiment, this embodiment is relatively weak during insertion due to the shear loads on the plank members during the insertion, which loads are absorbed by the pins.

Figure 46:
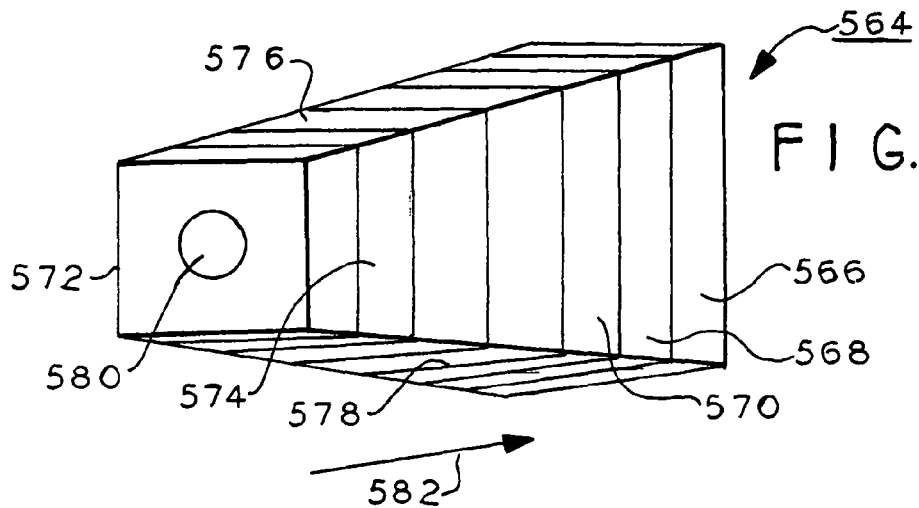

In FIG. 46, implant 564 comprises a plurality of axial stacked planks 566, 568 570 and so on generally of the same thickness, but this is not critical. The planks 566 and so on are square or rectangular in plan view in accordance with a given implementation. In this embodiment, the planks are square. The opposing side surfaces 572 and 574 are parallel and the opposing top and bottom surfaces 576 and 578 are flat and tapered to form the implant in a wedge shape. The planks may be formed as discussed in respect of the FIG. 87 embodiment. The fibers of the planks extend in the longitudinal direction of the pin 580. A single axially extending pin 580 passes through all of the planks.

The pin is preferably press fit in this embodiment as there is no second pin provided to resist sideway slippage of the plank layers due to compressive forces of a bent pin. Also, the various layers are also preferably bonded to each other to enhance the joining of the layers. The pin in the alternative may have the different shapes as discussed above to assist in joining the planks. This orientation of the planks provides enhanced resistance to shearing forces during insertion of the implant in direction 582. In the alternative, two or more pins may be provided with one or more with offsets at each plate as described above. The fiber direction of the planks may be oriented normal to the insertion direction to provide increased resistance to insertion shearing forces.

The finished implant may have tapered upper and lower surfaces as well as tapered sides. In addition, a chamfered end may be provided the insertion end of the implant to facilitate insertion. In addition, surface features such as holes, threads, slots and so on can be provided for an insertion tool (not shown). This implant is strong in supporting insertion loads and during use for supporting spinal compression loads. It is easy to fabricate and if the segments separate after insertion, spinal support would be largely unaffected.

A band saw presently available with a table guide is capable of holding 0.0762 mm (0.003 inch) tolerances for fabricating such planks or in the alternative, a table saw can be used to cut planks from femoral rings. It is less desirable to cut strips from cortical strips or from long bone segments. Retaining pins preferably are friction fit attached as described herein.

Figure 47:
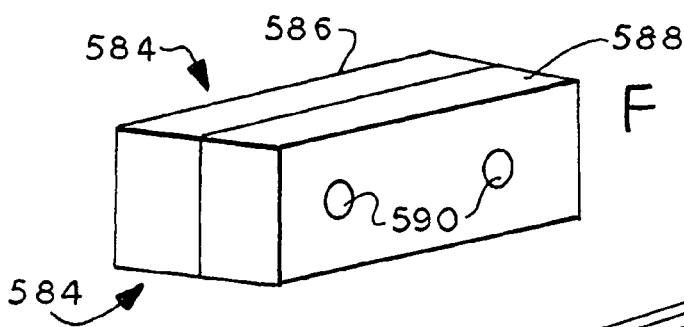

FIG. 47 illustrates an implant 584 comprising two planks 586 and 588 of cortical bone pinned by two horizontal pins 590. This implant is rectangular on all sides. The joint between the planks is vertical when inserted into the disc space. The pins and mating bores are as described above for the other embodiments.

Figure 48:
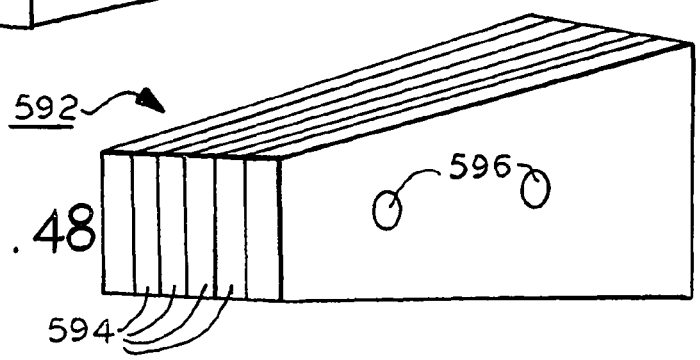

In FIG. 48, implant 592 comprises a stack of vertically oriented planks 594 preferably of the same thickness and which is not critical. Two pins 596 connect the planks. The pins pass through all of the planks as preferably occurs in all of the embodiments herein. The pins are attached by offsets or by different shapes and angles as discussed above. The advantages of this implant are similar to those in regard to the implant 564 of FIG. 46 and the disadvantages are as discussed with respect to the implant of FIG. 44.

With respect to fiber orientation in the planks of the implants of the different embodiments, it is preferred the orientation of the plank of FIG. 48 be utilized when two pins are used to prevent spreading of any splits which might occur and which splits do not adversely affect the compression loading of the implant in this and related embodiments utilizing vertically oriented planks as in implant 592.

Figure 49:
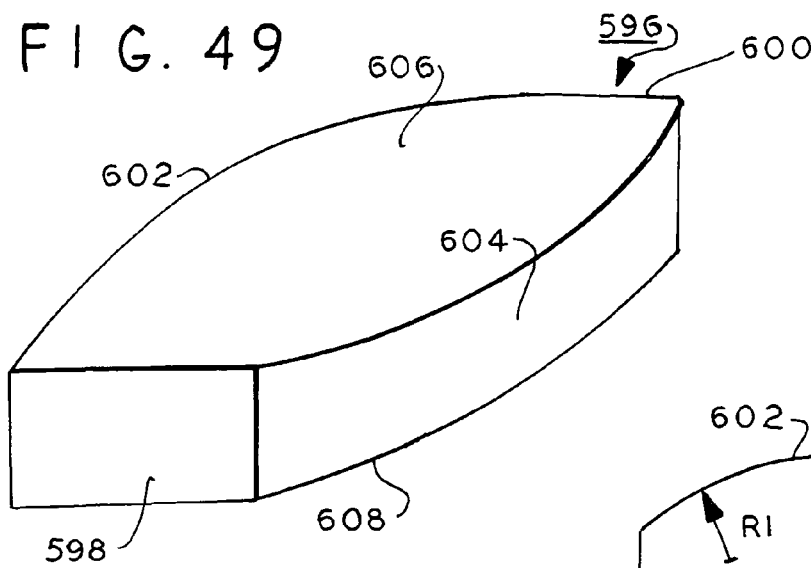
Figure 50:
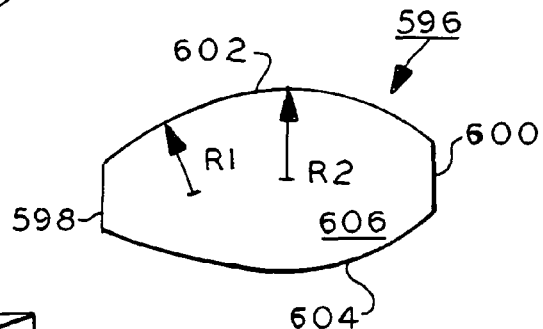
FIGS. 50 and 51 are respective top plan and side elevation views of the implant of FIG. 49.
Figure 51:
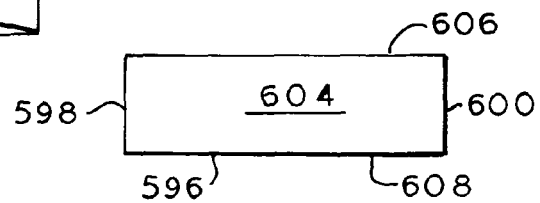

The implant 596 of FIGS. 49-51 is made of one piece cortical bone. It has a posterior end 598 and an anterior end 600. In plan view in FIG. 50, ends 598 and 600 are the same in cross sectional area and shape. The implant is of uniform thickness. It has two opposing sides 602 and 604 which are mirror images of each other. It also has two opposing upper and lower vertebra engaging surfaces 606 and 608, respectively. Sides 602 and 604 are convex and preferably elliptical. However, they may be formed as complex curves of multiple radii such as R1 and R2, FIG. 50. the surfaces 606 and 608 may be roughened or be grooved.

Figure 52:
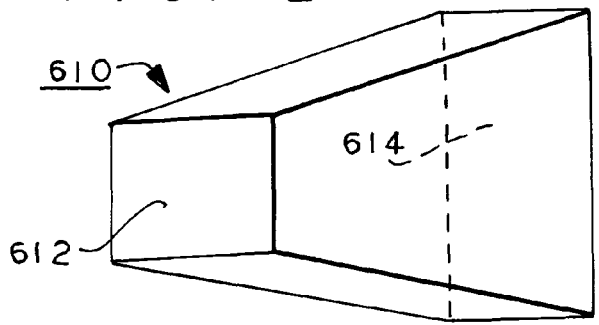

In FIG. 52, implant 610 has a square or rectangular posterior end 612 and a square or rectangular anterior end 614. All surfaces taper and converge toward end 612 forming a trapezoid shape from a normal view of that side. This implant is fabricated of one piece cortical bone or may comprise stacked layers of planks as in the above embodiments.

Figure 53:
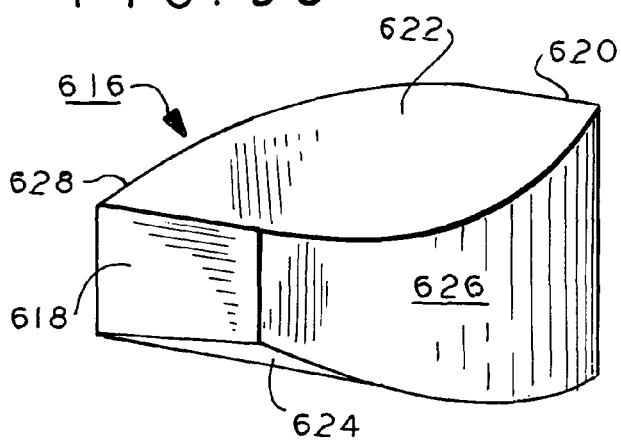
Figure 54:
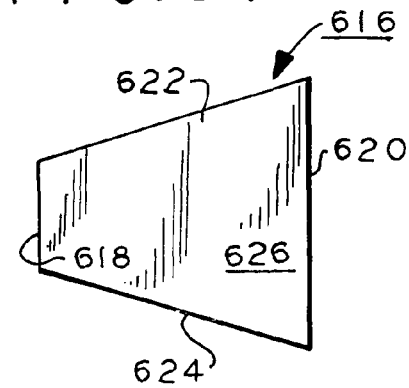
FIG. 54 is a side elevation view of the implant of FIG. 53.

In FIG. 53, implant 616 comprises a one piece cortical bone having posterior end 618 and anterior end 620. Implant 616 has a top vertebrae engaging surface 622 and a bottom vertebrae engaging surface 624. Implant 616 appears the same as implant 596, FIG. 50 in top plan view. The sides 626 and 628 are convex curved in the form of a segment of an ellipse or multiple radii of different values as in the embodiment of FIG. 50. The difference between implant 596 and implant 616 is that the surfaces 622 and 624 taper toward each other as seen in FIG. 54 so that the implant appears trapezoidal in side view. These shapes accommodate different disc spaces that may be encountered during surgery.

Figure 66:
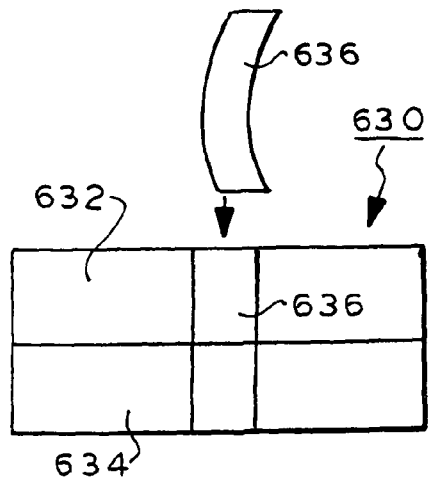
FIG. 66 is an exploded view of an implant and locking pin according to an embodiment of the present invention using the pin of FIG. 23.
Figure 67:
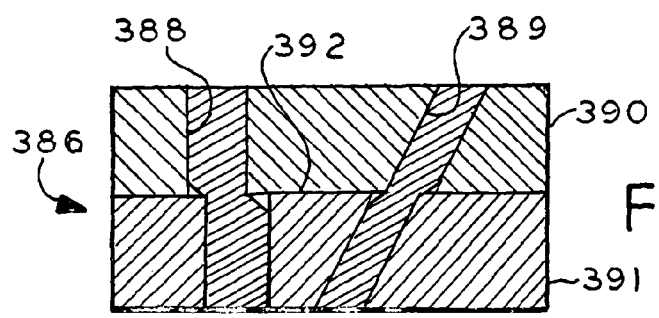

In FIG. 66 an implant 630 comprises two planks 632 and 634 as discussed in connection with the FIG. 1 and certain of the related embodiments above. However, the implant 630 has a straight through bore 636 which is formed by axially aligned bores of the same diameter in each of the planks 632 and 634. A curved pin 638 is forced into the bore 636. The curvature of the pin is such that the ends of the pin must bend into coaxial alignment in order to be inserted in to the bore 636. This bending introduces compression and tension forces in the pin which is transferred into compression forces in the planks 632 and 634 directed in the plane of the planks. These forces hold and lock the planks to the pin. The fiber directions in the elements is as described for the other embodiments.

In FIG. 75, implant 638 comprises two cortical bone planks 640 and 642. Two cortical bone pins 644, 645 are attached to mating bores normal to the interfaces 646 and 647 of the planks. The pins may be as described above herein in connection with any of the embodiments of the pin arrangements but preferably employ the offset arrangement of FIG. 4. The interface surfaces 646 and 647 of the planks have a respective complementary dovetail groove 648 and dovetail projection 649 formed therein for mechanically locking the two planks together. The dovetail joint extends in the longitudinal axial direction of the planks of axis 650. The implant 638 is shown rectangular in overall shape but may be other shapes as described above for the other embodiments.

In FIG. 76, implant 651 comprises two planks 652 and 653 of cortical bone having a longitudinal axis 656 joined by two cortical bone pins 654, 655 attached to mating bores normal to the interfaces 646 and 647 of the planks. The pins may be as described above herein in connection with any of the embodiments of the pin arrangements, but preferably employ the offset arrangement of FIG. 4. The interface surfaces of the planks have a respective complementary saw teeth and grooves 657 for mechanically securing the two planks from relative displacement in directions 658. The teeth and grooves extend in the longitudinal axial direction of the planks of axis 656. The implant 651 is shown rectangular in overall shape but may be other shapes as described above for the other embodiments.

In FIG. 77, implant 660 comprises two planks 661 and 662 of cortical bone having a longitudinal axis 664 joined by one cortical bone pin 665 attached to mating bores normal to the plane of the interface surfaces of the planks lying in axis 664. The pin may be as described above herein in connection with any of the embodiments of the pin arrangements, but preferably employs the offset arrangement of FIG. 4. The interface surfaces of the planks have respective complementary saw teeth and grooves 666 for mechanically securing the two planks from relative displacement in directions 667 along the axis 664. The teeth and grooves extend normal to the longitudinal axial direction of the planks of axis 664. The implant 651 is shown rectangular in overall shape but may be other shapes as described above for the other embodiments. The pin 665 has an offset or in the alternative, the mating bores in the two planks 661 and 662 are offset as shown in FIG. 4. In this embodiment, the direction of the offset of the bores 668 and 669, FIG. 77a, (or of the pin sections) is in directions 667. In this way the compression loads of the offset bent pin 665 are in the axial direction of axis 664 and slippage of the planks 661 and 662 in this direction due to such compression loads induced by the bent pin is precluded by the interengaged teeth and grooves 666. Similarly, a single pin may be used in the embodiment of FIG. 76 in which the offset is directed to impose relative slippage forces between the planks 652 and 653 in the directions 658 which is resisted by the engaged teeth and grooves 657.

Figure 78:
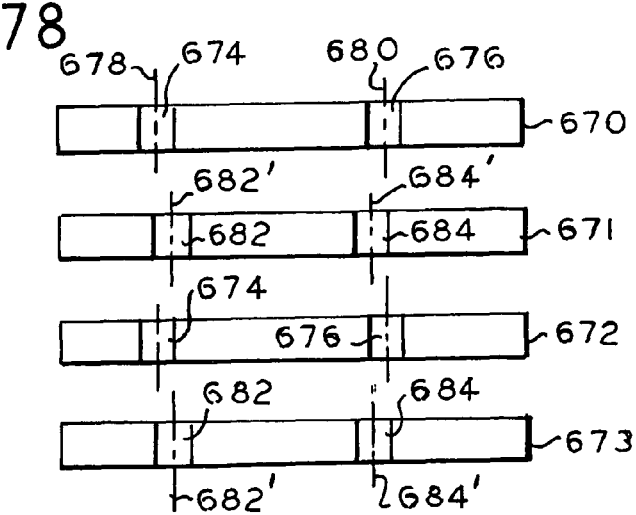
FIG. 78 is an exploded view of a stack of planks for forming an implant according to a further embodiment.

In FIG. 78, an array of cortical bone planks 670, 671, 672, 673 and 674 are shown in exploded view to show their stacked relation when joined. These planks have external dimensions that are preferably identical for purposes of illustration, but need not be according to a given implementation. These planks are rectangular in plan view but also may be other shapes as well. These planks are shown for purposes of illustrating the relationship of offset bores in stacked planks for receiving locking pins that are straight right circular cylinders of cortical bone.

Plank 670 is identical to plank 672 and plank 671 is identical to plank 673 in respect of the pin bores and their spaced relations. Plank 70 has two pin bores 674 and 676 which for purpose of illustration are identical and are right circular cylinders lying on respective axes 678 and 680. Plank 672 also has a set of bores 674 and 676 on respective axes 678 and 680. Plank 671 is between planks 670 and 672 and has bores 682 and 684 on respective axes 682' and 684'. Axes 682' and 684' are offset from respective axes 678 and 680 in opposing directions the same amount. In this embodiment, the axes 682' and 684' are closer together than axes 678 and 680 but in the alternative could be further apart. Similarly, plank 673 has a set of bores 682 and 684 on respective axes 682' and 684'.

Planks 670-673 are mounted together in abutting relation and may be bonded by an adhesive as described in the aforementioned U.S. Pat. No. 5,899,939. The planks are mechanically joined by two identical pins such as pin 243, FIG. 22, of appropriate length so that the ends of the pin are preferably flush with the outer exposed surface of planks 670 and 673.

The two pins are bent by the offset of the bores in the planks 670-673 is in opposing directions in any given corresponding plane parallel to the plane of the planks. The pins thus exhibit multiple compression and tensile loads normal to the plane of the planks. These compressive and tensile loads translate into compression load components in the plane of the planks in opposite directions, frictionally locking the planks to the pins. The pins are nominally the same diameter as the bores in the planks so that only compressive loads in one direction is imposed on each plank. This single compressive load direction minimizes the tendency of the planks to split along there fiber lengths as discussed in connection with FIGS. 80 and 82. The overall shape of the implant may be further machined to the desired surface configuration for a given implementation.

Figure 93:
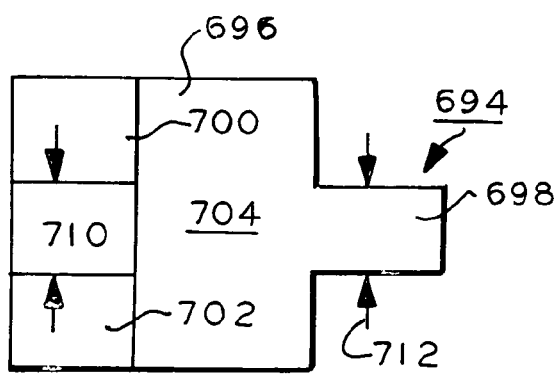
FIG. 93 is a representative side elevation view of one of the pieces of FIGS. 91 and 92.

In FIGS. 90-93, an implant 690 comprises two identical cortical bone pieces 692 and 694. These pieces interlock. Parts that have reference numerals that are primed in piece 692 are identical to parts with the same unprimed reference numeral in piece 694. Piece 694, FIGS. 92 and 93, comprises a body 696, which may be square in plan view as seen in FIG. 93 or rectangular, from which a projection 698 extends. The projection 698 may also be square or rectangular in plan view. Thicknesses are exaggerated in the figures for purposes of illustration, the overall dimensions of the implant being in the ranges discussed in connection with the embodiment FIG. 1.

Two like spaced projections 700 and 702 extend from a side 704 of body 696. The projections 700 and 702 may be identical and extend from the side 704 the same distance 708 as the thickness 706' of the projection 698 (and thickness 706' and 706 of the respective bodies 696' and 696). The body 696 has the thickness 706 throughout. The spacing 710 between the projections 700 and 702 is the same as the height dimension 712 of the projection 698.

Figure 90:
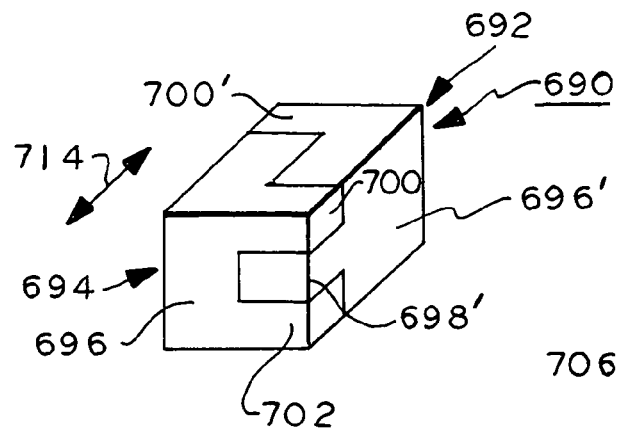
FIG. 90 is an isometric view of an implant according to a further embodiment.
Figure 91:
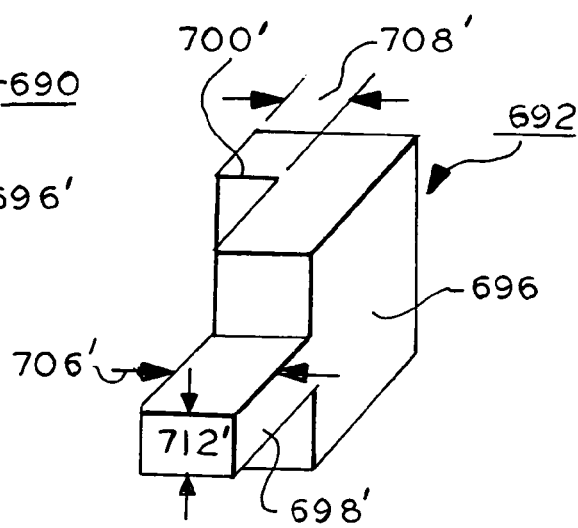
FIGS. 91 and 92 are isometric views of the identical pieces forming the implant of FIG. 90.
Figure 92:
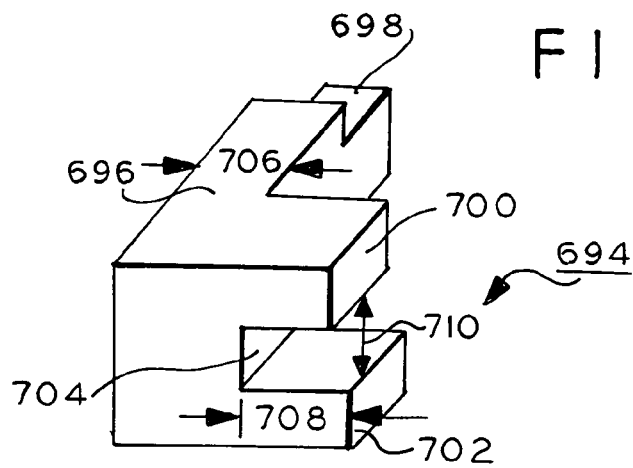

The projections 700 and 702 straddle and receive therebetween the projection 698', FIG. 90. The projections 700' and 702' (not shown) straddle and receive therebetween the projection 698. The two pieces 692 and 694 thus interlock and fit in close relation to form a solid block of bone forming a solid rectangular polygon figure elongated in directions 714. This implant 690, FIG. 90, thus has the overall appearance of implant 638 (FIG. 75), implant 651 (FIG. 76), implant 660 (FIG. 77), and the implants shown in FIG. 47 and in FIGS. 62-67. These implants may be further shaped as shown in the other embodiments to have tapering surfaces, ridges or saw teeth for gripping the engaged vertebra, chamfers for assisting in insertion and insertion tool complementary surface features, locking pins, interengaging saw teeth and so on.

Figure 94A:
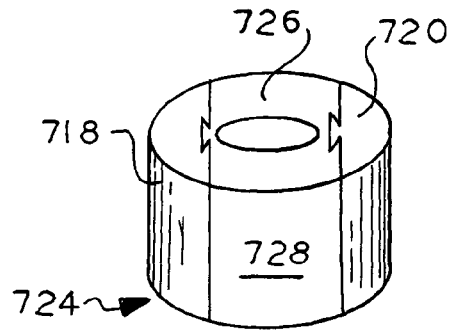
FIGS. 94a and 94b are isometric views of implants of further embodiments.
Figure 94B:
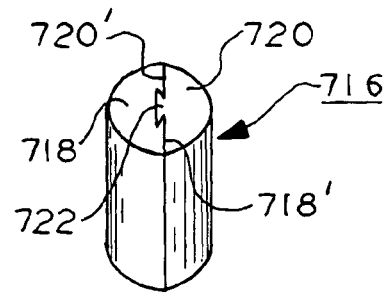

In FIG. 94b, implant 716 is oval in overall plan view looking from the top of the figure to the bottom. The implant 716 comprises two pieces 718 and 720. Each piece has a planar interface surface 718' and 720' respectively. The two pieces have a mating elements of a dovetail joint 722 comprising a dovetail projection and a dovetail groove. The dovetail joint interlocks the two pieces into a single implant structure similar to that described in FIG. 75. Offset pins (not shown) are optional. It should be understood that the term offset as applied to the pins means that either the pins are stepped and have axially offset portions as pin 90 or the pins are not straight, such as the pins in FIGS. 23 and 31 for insertion into a straight bore. Also the term offset as applied to the bores means the bores either are not straight, for receiving a straight pin or non-straight pin, or are stepped, as described above herein in FIG. 2 for example.

In FIG. 94a, the pieces 718 and 720 are fabricated from a cortical bone ring 724, the ring being formed as shown in connection with FIGS. 55 and 56. the fiber direction is vertical running from the top to bottom of the drawing figure. The remaining sections 726 and 728 of the ring 724 may be used to form planks, pins, screws and so on. A bone screw may have one or more helical threads. It should be understood that the shape of the implant 716 shown is schematic and in practice its final shape would conform to the desired shape and dimensions needed for insertion in a given spinal disc space or other insertion space.

Figure 95:
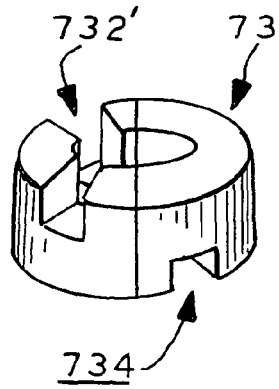
FIG. 95 is an isometric view of a cortical bone ring partially processed for forming the implant of FIGS. 97 and 98.
Figure 96:
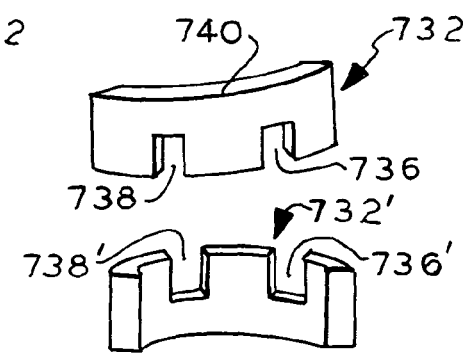
FIG. 96 is an exploded side isometric view of the bone pieces formed from the ring of FIG. 95 prior to assembly.
Figure 97:
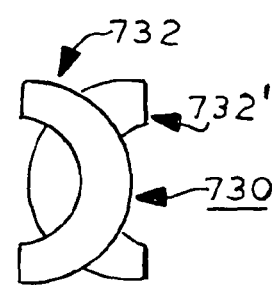
FIGS. 97 and 98 are respective top plan and side elevation views of an implant formed by the pieces of FIG. 96.
Figure 98:
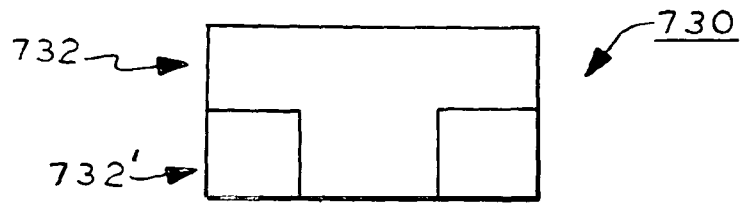

In FIGS. 97-98, implant 730 comprises two mirror image identical pieces 732, 732'. Pieces 732 and 732' are fabricated from cortical bone ring 734, FIG. 95. The two pieces are each semi-circular and formed from a half of circular cylindrical ring 734 which is machined to the exterior shape. The central open core may also be machined by broaching for example to form a central circular cylindrical opening in the medullary canal of a long bone. Representative piece 732 has Identical slots 736 and 738 formed in the body 740.

In the assembly, the slots 736 and 736' of the two pieces are interengaged. The slots 738 and 738' of the two pieces are also interengaged at the same time. The resulting interlocked assembly is shown in FIGS. 97 and 98. The two pieces preferably are bonded together with a suitable adhesive. The external surfaces may be tapered, chamfered and grooved according to a given implementation.

In respect of producing pins, the pins may be in interference fit or offset. The pins are preferably formed from under utilized bone scrap left over from plank manufacturing from larger bones using a hole or core saw. Each pinned implant blank is machined to a finished implant including interface features for insertion tools. Conventional milling techniques may be used to fabricate the various pieces of the different embodiments. Surface features such as saw teeth or projections and grooves are used to transmit loads and hold the pieces together as needed.

Figure 99:
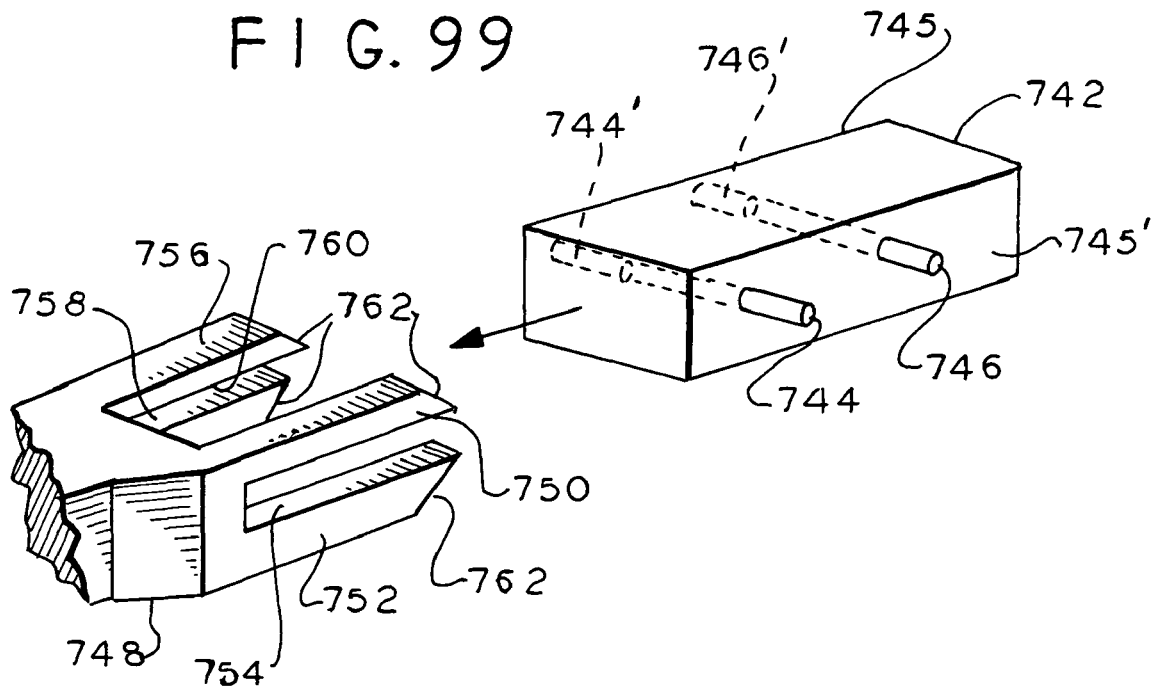
FIG. 99 is an isometric exploded view of an implant inserter tool and bone implant for use with the inserter.

In FIG. 99, implant 742 is shown by way of example for illustration as a rectangular block of bone, but in practice may be of any shape or configuration, solid or hollow, as described hereinabove. The implant 742 has two parallel pins 744 and 746 passing therethrough and extend beyond opposite sides of the implant. The pins are secured in mating bores as described above. In the alternative, the pins 744 and 746 may comprise four separate pins, for example, pin portions 744' and 746' extending from side 745 of the implant, each pin extending from a blind bore (not shown) in the opposing sides 745, 745' of the implant 742.

An implant insertion tool 748 includes a pair of mating spaced aligned tines 750, 752 on one side of the tool 748. Tines 750, 752 form a slot 754 therebetween. The slot 754 is dimensioned to receive the protruding pin portions of pins 744 and 746 in sliding close fit therewith.

Figure 100:
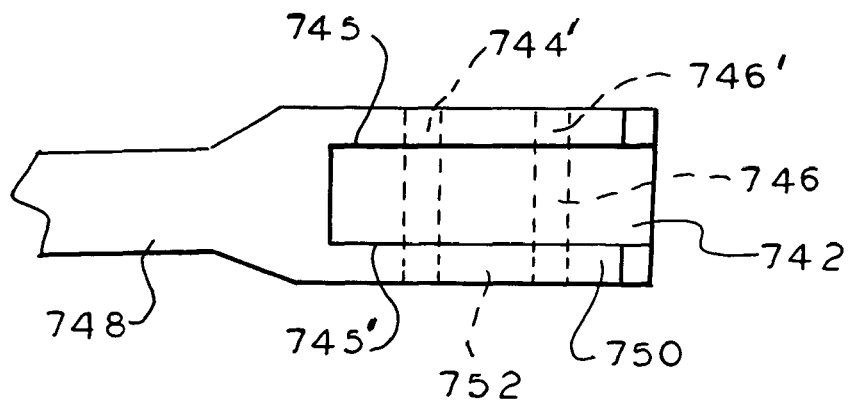
FIG. 100 is a top plan view of the inserter and implant of FIG. 99 assembled showing the temporary attachment of the inserter and implant.

The insertion tool 748 has a second pair of tines 756 and 758 which define a slot 760 on a side of the tool opposite the tines 750 and 752. Slot 760 receives the pin portions 744', 746' of pins 744 and 746 protruding from the opposite side of the implant 742. The tool 748 of FIG. 100 shows the implant pins assembled to the tool slots 754 and 760. The tips 762 of the tines may be chamfered to facilitate insertion of the tool into the disc space of a patient's spine. The chamfers are inclined in opposite directions relative to each other on each pair 750, 752 and 756, 758 to form a wedge shaped leading edge with the implant. The pins 744 and 746 may be of any of the shapes and configurations as described above herein. The tool 748 and implant 742 with the protruding pins helps keep the implant from twisting during insertion.

It will occur to one of ordinary skill that modifications may be made to the disclosed embodiments without departing from the scope of the invention as defined in the appended claims. The disclosed embodiments are given by way of illustration and not limitation. For example, while bone pins are preferred, pins of other known biocompatible materials may be used for the implant planks. Also, the planks and implants may be formed of non-bone biocompatible materials.

What is claimed is:

1. A method of forming a bone implant comprising:
    assembling two cortical bone planks in parallel abutting relation;
    boring at least one first bore in one of the bone planks in a first direction; and
    boring at least one second bore in the other of the bone planks in a second direction generally opposite the first direction wherein the first and second bores are offset relative to each an amount such that a straight bone pin inserted into the first bore and through to the second bore is placed in compression and tension.

2. The method of claim 1 wherein the bores have parallel axes.

3. The method of claim 1 wherein the offset of the axes is in the range of about 0.1-10 mm.

4. A method of forming an implant comprising:
    forming first and second cortical bone planks;
    forming a bore in each said planks; and
    inserting a bone pin in the bores so as to cause the pin to exhibit both compressive and tensile loads which compressively secure the planks to the pin; the bores and pin being arranged so that the pin exhibits compressive and tensile forces for applying a compressive load on the planks, one of (1) one section of the pin having an outer peripheral diametrical surface that is offset relative to a second pin section outer peripheral diametrical surface and (2) the bores in at least two of said planks being offset relative to each other for creating said compressive and tensile forces.

5. The method of claim 4 including forming the pin from cortical bone exhibiting a fiber direction, the pin having a length dimension, the fiber extending in the length direction.

6. The method of claim 4 including surface demineralizing the bores.

7. The method of claim 4 including demineralizing at least the surface of said pin.

8. The method of claim 4 including surface demineralize said bores and said pin.

9. The method of claim 4 including fully demineralizing at least a portion of the pin and surface demineralizing the implant and said bores.

* * * * *